(12) United States Patent
Forrest et al.

(10) Patent No.: US 8,802,235 B2
(45) Date of Patent: Aug. 12, 2014

(54) DRUG AND IMAGING AGENT DELIVERY COMPOSITIONS AND METHODS

(71) Applicant: University of Kansas, Lawrence, KS (US)

(72) Inventors: Marcus Laird Forrest, Lawrence, KS (US); Shaofeng Duan, Lawrence, KS (US); Shuang Cai, Lawrence, KS (US); Ti Zhang, Lawrence, KS (US); Qiuhong Yang, Lawrence, KS (US); Daniel Aires, Prairie Village, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 13/745,167

(22) Filed: Jan. 18, 2013

(65) Prior Publication Data

US 2013/0189519 A1    Jul. 25, 2013

Related U.S. Application Data

(60) Provisional application No. 61/588,047, filed on Jan. 18, 2012, provisional application No. 61/588,508, filed on Jan. 19, 2012.

(51) Int. Cl.
*B32B 5/16* (2006.01)

(52) U.S. Cl.
USPC .......................................................... 428/402

(58) Field of Classification Search
USPC .............. 560/147, 151; 428/402; 526/238.23, 526/289; 525/328.5, 327.2
See application file for complete search history.

(56) References Cited

U.S. PATENT DOCUMENTS

2005/0272617 A1    12/2005    Camenzind et al.
2011/0060036 A1    3/2011    Nie et al.

FOREIGN PATENT DOCUMENTS

WO    WO 2011/115641    9/2011
WO    WO 2011/130694    11/2011

OTHER PUBLICATIONS

Tanton et al. (Direct Synthetic Strategies to Hydrophilic Starlike Polymers by MADIX, in Controlled/Living Radical Polymerization; Matyjaszewski, K.; ACS Symposium Series; American Chemical Society: Washington, DC, 2006).*
Schurink (Pentaerythritol, Org. Synth. 1925, 4, Org. Synth. 1941, Coll. vol. 1).*
Qiu et al. (Polymer Architecture and drug Delivery, Pharmaceutical Research, 2006).*
Yu et al. (Study of Glucose Ester Synthesis by Immobilized Lipase from *candida* sp., Catalysts Communications, 9, 1369-1374, 2008).*
Simoneit et al. (Sugars-Dominant Water-Soluble Organic Compounds in Soils and Characterization as tracers in atmospheric Particulate Matter, Environ. Sci. Technol, 38, 5939-5949, 2004).*
Chakrapani et al. (Synthesis and in vitro anti-leukemic activity of structural analogues of JS-K, an anti-cancer lead compound, Bioorganic & Medicinal Chemistry Letters 18 950-953 , 2008).*
Schimpf et al. (Measurement of Polydispersity of Ultra-Narrow polymer Fractions by thermal Field-Flow Fractionation, Journal of Applied Science, vol. 33, 117-135, 1987).*
International Search Report/Written Opinion from related PCT Application PCT/US2013/022169 dated Apr. 10, 2013 (8 pgs).

* cited by examiner

*Primary Examiner* — Brandon Fetterolf
*Assistant Examiner* — Blaine G Doletski
(74) *Attorney, Agent, or Firm* — Stinson Leonard Street LLP

(57) ABSTRACT

A multi-arm, star-shaped polymer composition can be configured for drug delivery and imaging applications in vivo. The star polymer architecture can be synthesized using living radical polymerization techniques, including reversible addition-fragmentation chain transfer and macromolecular design via the interchange of xanthates with a broad range of reaction conditions and functional groups. The star-shaped polymeric carriers can be tailored for preferential delivery of chemotherapeutics into the tumor-draining lymphatics via subcutaneous, peritumoral or intratumoral injections. The carriers can be loaded with the chemotherapeutic agents from about 10% to about 25% w/w. In addition, the carriers can be loaded with imaging agents from about 5% to about 10% w/w. The molecular weights of the polymeric carriers can be about 40 kDa to about 130 kDa. The chemotherapeutics can be cisplatin, geldanamycin or nitric oxide-donating prodrugs. The imaging agent can be a near-infrared dye, such as IR820.

19 Claims, 17 Drawing Sheets

DRUG AND IMAGING AGENT DELIVERY COMPOSITIONS AND METHODS

CROSS-REFERENCE

This patent application claims benefit of U.S. provisional patent application 61/588,047, filed Jan. 18, 2012 and U.S. provisional application 61/588,508 filed on Jan. 19, 2012, which provisional applications are both incorporated herein by specific reference in their entirety.

BACKGROUND OF THE INVENTION

Multi-arm or star polymer architectures are a new generation of branched polymeric materials that include a single core and multiple connecting arms or chains. Star polymers usually have highly condensed and globular structures, tailorable size and large surface areas for conjugation of therapeutic agents and imaging agents, which makes them suited as potential delivery platforms. Various star polymer carriers have been synthesized and utilized for the delivery of small-molecule chemotherapeutics, including doxorubicin (conjugation) and paclitaxel (encapsulation), proteins, such as insulin, as well as genetic materials, such as DNAs and siRNAs.

Multi-arm polymers can be synthesized under a broad range of conditions with low polydispersity using reversible addition-fragmentation chain transfer polymerization (RAFT). During the RAFT process, the polymers derived keep their "livingness" so that it is possible to prepare well-defined polymers. Moreover, the RAFT process is tolerant toward a range of functional groups thus minimizing the need for additional synthetic pathways to install protecting groups on the monomers being used.

Nitric oxide is a cell signaling molecule involved in many mammalian physiological processes and pathological conditions. The effects of nitric oxide on tissues are highly concentration dependent. Low levels of nitric oxide synthase (NOS) overexpression in cancer cells is frequently associated with enhanced tumor cell invasion and growth and an increase in aerobic glycolysis capacity, i.e., the Warburg effect. However, high concentrations of nitric oxide can inhibit NF-kB activity, which regulates cell proliferation, and down-regulating Bcl-xL expression, which modulates apoptotic pathways. Nitric oxide has been shown to radio-sensitize cancers, inhibit DNA repair mechanisms, inhibit hypoxia-induced drug resistance, and reverse the epithelia to mesenchyma phenotype transition of tumors. Nitric oxide has a half-life of about 5 seconds in vivo, due to rapid reaction of the unpaired electron with hemoglobin and heme-ferrous iron and subsequent decomposition into nitrate. Therefore, nitric oxide donating pro-drugs have been developed for anti-cancer therapy, such as JS-K. JS-K is a glutathione S-transferase-activated (GST-activated) nitric oxide prodrug, releasing nitric oxide in vitro, inhibiting the proliferation of cancer cells, including breast cancer cells, non-small-cell lung cancer cells and myeloma cells. Because GSTs are also expressed in normal mammalian organs, the potential toxicity and carcinogenicity of JS-K must not be overlooked.

The potential for dose-dependent carcinogenicity of nitric oxide-releasing agents has limited their development as systemically administered anti-cancer agents. The effective and safe use of these agents requires that the nitric oxide release be highly confined to tumorigenic tissues and exposure to sub-therapeutic doses must be minimized. The tissue distribution of small molecule drugs is typically non-specific, with increased exposure in clearance organs, such as the kidneys and liver. To overcome this challenge, a drug molecule may be conjugated to a targeted delivery system so that it will be preferentially released in tumorigenic cells. Water-soluble polymers have been utilized for the preparation of drug conjugates that display significant advantages in pharmaceutical applications, including low toxicity, excellent water solubility, and tissue targeting through passive (e.g., enhanced permeation and retention effect) or receptor-based targeting. Despite the targeted nature of these carriers in intravenous applications, healthy tissues will still receive substantial exposure due to long residence in the clearance organs and circulatory system. This problem can be partially overcome by delivering nanoconjugates directly to the primary tumor and the draining lymphatics. This approach can greatly improve the response in locally advanced cancers, since the nanoconjugate and method of administration can confine the drug to only the tumor and the lymph nodes draining the tumor. An issue in the design of these drug delivery systems is the carrier must be very stable within the extravascular space, which limits the use of micelles and liposomes, and it should be under 50 nm in size for rapid clearance from the injection site. Structured polymers such as dendrimers meet these requirements, but dendrimers such as polyamidoamine (PAMAM) constructs are not biodegradable and have limited capacity for water-insoluble drugs. Multi-arm or star polymers are branched nanoscale materials that have a compact structure, globular shape, and large surface area that make them highly suited for targeted drug delivery when built with non-toxic and biodegradable polymers.

Cisplatin is a water soluble, platinum-based chemotherapeutic that has been widely used for many years in the clinic as a first-line chemotherapy for head and neck squamous cell carcinoma, ovarian cancer, and non-small cell lung cancer. The major side effect of cisplatin infusion chemotherapy is renal toxicity, which limits its use. The toxicity of cisplatin is dependent on the maximum concentration of free drug in the plasma. Slow and confined release of cisplatin into tumors can largely alleviate these toxicities.

Geldanamycin (GA), an ansamycin benzoquinone antibiotic, is an HSP90 inhibitor that exhibits both antimicrobial activity and anticancer activity. The anti-cancer activity of GA was first determined in the 1970s against L1210 murine leukemia and KB cells; despite its encouraging in vitro and in vivo activity in early preclinical studies, its development was limited due to its significant hepatotoxicity in vivo. Nevertheless, two of its C-17 analogues, 17-allylamino-17-demethoxygeldanamycin (17-AAG) and 17-dimethylaminoethylamino-17-demethoxygeldanamycin (17-DMAG), have been pursued in the clinic due to their enhanced activity, decreased liver toxicity, and increased water solubility (17-DMAG). Further, 17-AAG was found to have efficacy in both HER2 positive (SKBr3) and negative (MCF7) breast cancer cell lines, and deplete the HER2 oncoprotein in the SKBr3 cell line. Due to its increased water solubility and equivalent activity, the development of 17-DMAG over 17-AAG has grown in interest. With the combined reports of HSP90 overexpression in melanoma, its function in the metastasis of melanoma, and activity against HER2 positive breast cancer, a lymphatically targeted geldanamycin derivative-star polymer conjugate was developed for the localized delivery to both locally advanced melanoma and breast cancers.

Charge is an important factor for lymphatic uptake of nanoparticles. Studies with proteins, liposomes, dendrimers, and PLGA-nanospheres have demonstrated that negatively charged particles have increased lymphatic uptake compared to neutral to positively charged particles, due in part to the electrostatic repulsions between the negatively charged particles and the extracellular matrix, which is primarily negatively charged. Also, negatively charged particles are retained longer, and to a greater extent by lymph nodes. Manipulation of the size, molecular weight, charge, and surface chemistry of polymers, such as multi-arm polymers, may affect the pharmacokinetics and tissue distribution of these materials after injection, e.g., by in the intravenous, subcutaneous, peritumoral, percutaneous, interstitial, peri-tumoral, intraocular, intratumoral, submucosa, mucosa, intradermal, peritoneal, inhalation routes, or by pulmonary instillation, ingestion, transdermal application, or administration to cavities, tissues, organs, or spaces within the body.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 8A includes SEC traces of poly(tert-butyl acrylate) star polymers with molecular weights of 148,991, 115,697, and 93,891 Da. FIG. 8B includes SEC traces of poly(acrylic acid) star polymers with molecular weights of 86,073, 67,112, and 54,007 Da.

FIG. 9A is the $^1$H-NMR spectra of poly(tert-butyl acrylate) star polymer. The $^1$H-NMR ($CDCl_3$, 400 MHz): δ=4.65 (q, 8H), 4.25 (q, 4H), 4.03 (q, 8H), 2.25 (brs), 1.86 (brs), 1.65-1.27 (brs, overlap). FIG. 9B is the $^1$H-NMR spectra of poly(acrylic acid) star polymer. The $^1$H-NMR ($CDCl_3$, 400 MHz): $^1$H-NMR ($CDCl_3$, 400 MHz): δ=4.66 (q, 8H), 4.30 (q, 4H), 4.14 (q, 8H), 2.25 (brs), 1.86 (brs), 1.65-1.27 (brs, overlap), 1.30 (t, 12H).

FIG. 10A includes the viscosity measurements of poly(acrylic acid) star polymers at concentrations of 1, 3, and 10 mg/mL. FIG. 10B includes the viscosity measurement of star polymer nitric oxide prodrug conjugates (72.3 kDa).

FIG. 11A includes a graph of the release kinetics of platinum from poly(acrylic acid) star polymer-cisplatin conjugates in PBS at 37° C. (N=3). The release half-life was determined to be 120 days using a linear regression or a first order decay model in GraphPad 5. FIG. 11B includes a graph of the release kinetics of platinum from poly(acrylic acid) star polymer-cisplatin conjugates in PBS with 10% serum at 37° C. (N=3). The release half-life was determined to be 36.7 hours using a linear regression or a first order decay model in GraphPad 5.

FIG. 19A includes $^1$H-NMR spectra and SEC traces of multi-arm poly-(1,2:3,4-di-O-isopropylidene-6-O-methacryloyl-α-D-galactopyranose) ($M_n$=73,292 Da, PDI=1.13). FIG. 19B includes $^1$H-NMR spectra and SEC traces of multi-arm poly-(6-O-methacryloyl-D-galactose) ($M_n$=45,460 Da, PDI=1.20).

FIG. 21A includes a graph of the size measurement of head and neck tumors. FIG. 21B includes a graph of the survival rate of the animals. Treatment groups include: Sugar-NO1 (10 mg/kg dose on NO1 basis, s.c., N=11), JS-K (10 mg/kg dose, i.v., N=7) and treatment-free control (N=8). Errors were reported in standard error of the mean.

FIG. 25A includes an image after subcutaneous injections into the footpad of a mouse (top: popliteal node, bottom: iliac node) of 74 kDa star polymer-IR820 conjugates. FIG. 25B includes an image after subcutaneous injections into the forearm of a mouse (axillary lymph nodes) of 74 kD star polymer-IR820 conjugates.

FIG. 26A depicts the drainage kinetics to the popliteal lymph nodes after s.c. administration into the right hind footpad. FIG. 26B depicts the drainage kinetics to the iliac lymph nodes after s.c. administration into the right hind footpad. FIG. 26C depicts the area under the curve (AUC) of the acid-star-IR820 conjugates in the popliteal lymph nodes. FIG. 26D depicts the AUC of the acid-star-IR820 conjugates in the iliac lymph nodes.

FIG. 30A includes a graph of the B16F10 tumor growth in response to no treatment (red, n=4), 60% acid-star polymer (s.c. equivalent star polymer dose to Star-GA, purple, n=6), 17-DMAG (i.v. 15 mg/kg, blue, n=4), Star-GA (s.c. 15 mg/kg DMAG equivalent, green, n=7), or melphalan treatment (i.v. 5 mg/kg, black, n=3). FIG. 30B include a graph of the percent change in body weight in response to no treatment (red, n=5), 60% acid-star polymer (s.c., purple, n=7), 17-DMAG (i.v. blue, n=7), or Star-GA (s.c. green, n=8).

DETAILED DESCRIPTION OF THE INVENTION

Figure 1:
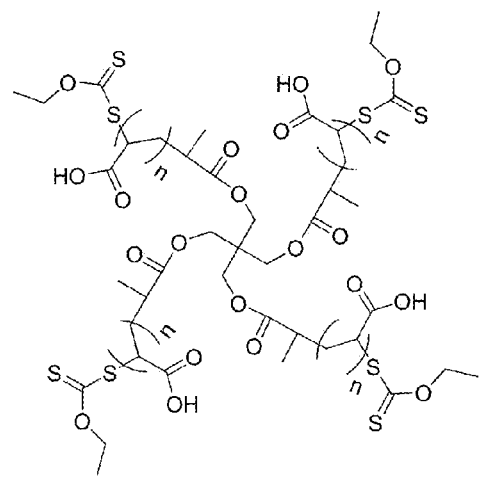
FIG. 1 includes a drawing of the chemical structure of multi-arm poly(acrylic acid) star polymer. The polymer was synthesize via a reversible addition-fragmentation chain transfer (RAFT) approach and modified with a macromolecular design via the interchange of xanthates (MADIX) method.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present invention is directed to multi-arm compounds. In one aspect, the multi-arm compounds are optionally conjugated to one or more therapeutic agents and/or imaging agents according to Formula 1:

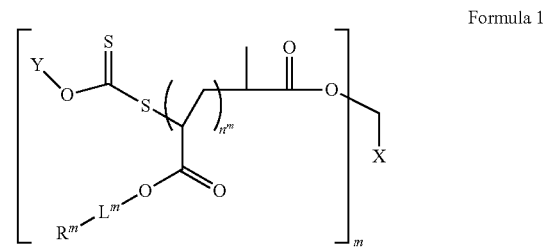

Formula 1 wherein X is one of carbon (C), oxygen (O), nitrogen (N), phosphorous (P), or sulfur (S); m is 2, 3, 4, 5, 6, 7, or 8; $L^m$ are each independently a bond or a linker; $R^m$ are each independently a therapeutic agent and/or imaging agent; Y is alkyl (preferably a $C_1$-$C_6$ alkyl, e.g. methyl, ethyl, propyl, etc); and $n^m$ are each independently an integer from 2 to 500 (e.g., 2, 3, 4, 5, 6, 7, 8, 9, 10, 12, 14, 16, 18, 20, 22, 24, 26, 28, 30, 35, 40, 45, 50, 55, 60, 65, 70, 75, 80, 85, 90, 100, 125, 150, 175, 200, 250, 300, 350, 400, 450, or 500); and wherein -$L^m$-$R^m$ together may be hydrogen (H). Thus, it will be appreciated that the multi-arm compounds of the present invention may or may not have a linker $L^m$. Likewise, the multi-arm compounds of the present invention may or may not be conjugated to therapeutic agent or imaging agent $R^m$.

In another aspect, the multi-arm compounds are optionally conjugated to one or more therapeutic agents and/or imaging agents according to Formula 1A:

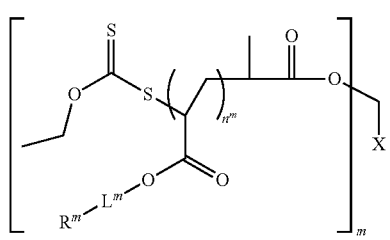

Formula 1A wherein X is one of carbon (C), oxygen (O), nitrogen (N), phosphorous (P), or sulfur (S); m is 2, 3, 4, 5, 6, 7, or 8; $L^m$ are each independently a bond or a linker; $R^m$ are each independently a therapeutic agent and/or imaging agent; and $n^m$ are each independently an integer from 2 to 500 (e.g., 2, 3, 4, 5, 6, 7, 8, 9, 10, 12, 14, 16, 18, 20, 22, 24, 26, 28, 30, 35, 40, 45, 50, 55, 60, 65, 70, 75, 80, 85, 90, 100, 125, 150, 175, 200, 250, 300, 350, 400, 450, or 500); and wherein -$L^m$-$R^m$ together may be hydrogen (H).

In another aspect, the present invention is directed to compounds having four arms according to Formula 1B:

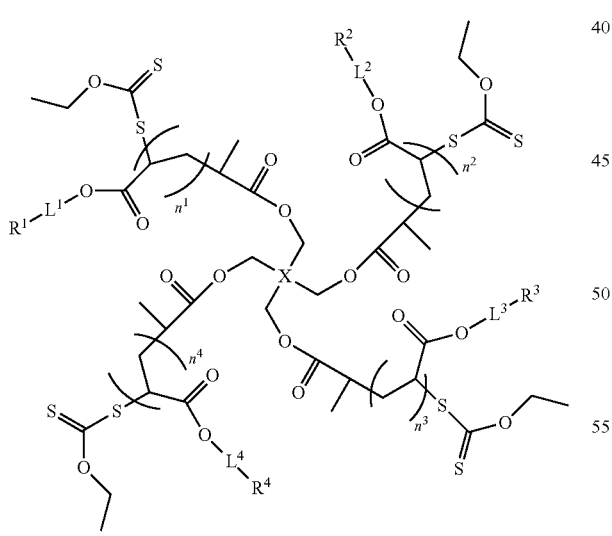

Formula 1B wherein X is one of carbon (C), phosphorous (P), or sulfur (S); $L^1$-$L^4$ are each independently a bond or a linker; $R^1$-$R^4$ are each independently a therapeutic agent and/or imaging agent; and $n^1$-$n^4$ are each independently an integer from 2 to 500.

In another aspect, the present invention is directed to compounds having four arms according to Formula 1C:

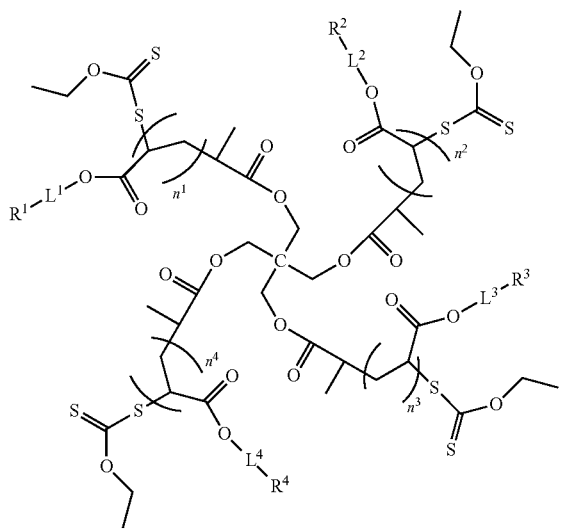

Formula 1C wherein $L^1$-$L^4$ are each independently a bond or a linker; $R^1$-$R^4$ are each independently a therapeutic agent and/or imaging agent; and $n^1$-$n^4$ are each independently an integer from 2 to 100 (e.g., 2, 3, 4, 5, 6, 7, 8, 9, 10, 12, 14, 16, 18, 20, 22, 24, 26, 28, 30, 35, 40, 45, 50, 55, 60, 65, 70, 75, 80, 85, 90, 100, 125, 150, 175, 200, 250, 300, 350, 400, 450, or 500).

In another aspect, the present invention is directed to compounds having four arms according to Formula 2:

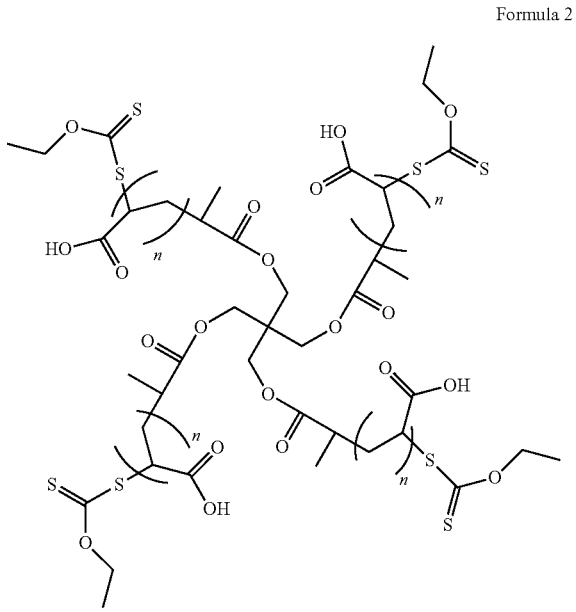

Formula 2 wherein n is an integer from 2 to 100 (e.g., 2, 3, 4, 5, 6, 7, 8, 9, 10, 12, 14, 16, 18, 20, 22, 24, 26, 28, 30, 35, 40, 45, 50, 55, 60, 65, 70, 75, 80, 85, 90, 100, 125, 150, 175, 200, 250, 300, 350, 400, 450, or 500).

In another aspect, the present invention is directed to compounds having four arms according to Formula 3:

Formula 3

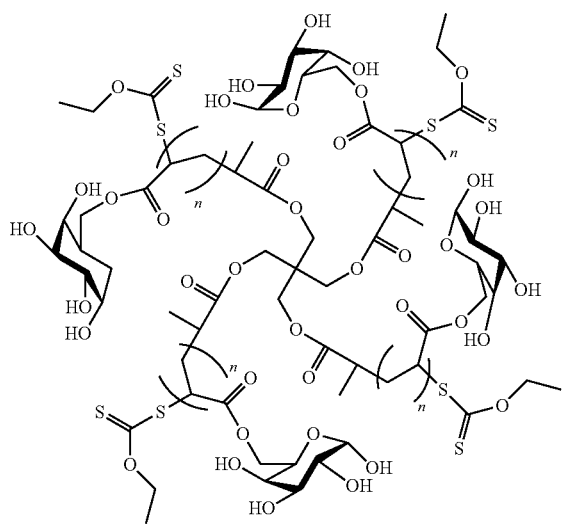

wherein n is an integer from 2 to 100 (e.g., 2, 3, 4, 5, 6, 7, 8, 9, 10, 12, 14, 16, 18, 20, 22, 24, 26, 28, 30, 35, 40, 45, 50, 55, 60, 65, 70, 75, 80, 85, 90, 100, 125, 150, 175, 200, 250, 300, 350, 400, 450, or 500).

Generally, a multi-arm, star-shaped polymer composition can be configured for drug delivery and/or imaging applications in vivo. The star polymer architecture may be synthesized using living radical polymerization techniques, including reversible addition-fragmentation chain transfer and macromolecular design via the interchange of xanthates with a broad range of reaction conditions and functional groups. The star-shaped polymeric carriers may be tailored for preferential delivery of chemotherapeutics into the tumor-draining lymphatics typically via subcutaneous, peritumoral or intratumoral injections. In one aspect, the carriers are loaded with chemotherapeutic agents, preferably from about 2% to about 40% w/w (e.g., about 2, 5, 10, 15, 20, 25, 30, 35, or 40 w/w %). In another aspect, the carriers are loaded with imaging agents, preferably about 5% to about 10% w/w (e.g., about 5, 6, 7, 8, 9, or 10 w/w %). The molecular weights of the polymeric carriers can be about 30 kDa to about 1 MDa (e.g., about 30, 40, 50, 60, 70, 80, 90, 100, 110, 120, 130, 140, 150, 200, 250, 300, 350, 400, 450, 500, 550, 600, 650, 700, 750, 800, 850, 900, 950, 1000 kDa). In one exemplary aspect, the chemotherapeutics are cisplatin or other platinum drugs (e.g. oxliplatin or its derivatives, carboplatin or its derivatives)), geldanamycin, rapamysin, taxanes, doxorubicin, alternol, TGX221, reactive oxygen species generators or nitric oxide-donating prodrugs. In another exemplary aspect, the imaging agent is a near-infrared dye, such as IR820, MRI contrast agents, e.g., gadolinium, or PET/CAT agents, e.g., 123I, or copper. These carriers impart high solubility and biocompatibility to the therapeutic agent and/or imaging agents.

The present invention provides improved delivery of therapeutic agents and imaging agents to cancers that metastasize lymphatically. The polymer can be made to any desired charge, can be conjugated to therapeutic agents in organic solution, it is less viscous for injection, and it is very soluble so it can incorporate more therapeutic agents.

In one aspect, multi-arm compounds of the present invention are poly(tert-butyl acrylate) star polymers having a molecular weight ranging from about 30 to 150 kDa (e.g., about 30, 40, 50, 60, 70, 80, 90, 100, 110, 120, 130, 140, or 150 kDa). Preferred molecular weights range from about 60 to 90 kD (e.g., about 60, 65, 70, 75, 80, 85, or 90 kDa). In another aspect, the poly(tert-butyl acrylate) star polymer has a polydispersity index (PDI) of about 1.1 to about 1.3 (e.g., about 1.1, 1.15, 1.2, 1.25, or 1.3).

In one aspect, multi-arm compounds of the present invention are poly(acrylic acid) star polymers having a molecular weight ranging from about 30 to 150 kDa (e.g., about 30, 40, 50, 60, 70, 80, 90, 100, 110, 120, 130, 140, or 150 kDa). Preferred molecular weights range from about 60 to 90 kD (e.g., about 60, 65, 70, 75, 80, 85, or 90 kDa). In another aspect, the poly(acrylic acid) star polymer has a PDI of about 1.1 to about 1.3 (e.g., about 1.1, 1.15, 1.2, 1.25, or 1.3).

In one aspect, multi-arm compounds of the present invention are sugar star polymers or an acid derivatives thereof having a molecular weight ranging from about 30 to 150 kDa (e.g., about 30, 40, 50, 60, 70, 80, 90, 100, 110, 120, 130, 140, or 150 kDa).

In one embodiment, the present invention includes a chemotherapeutic composition configured for local administration by percutaneous injection. The composition can include multi-arm or star polymer nanocarriers conjugated to the chemotherapeutic agent. The chemotherapeutic composition is preferably configured for preferential intralymphatic accumulation after percutaneous (where percutaneous encompasses subcutaneous, intratumoral, intradermal, peritumoral, submucosal, or transdermal) administration.

In one embodiment, the nanoconjugate can include multi-arm polymers and one or more therapeutic agents used for therapeutic purposes. In certain embodiment, the nanoconjugate can include a multi-arm polymer and one or more imaging agents, which provide for contrast in one or more imaging techniques, including but not limited to: photoacoustic imaging, fluorescence imaging, ultrasound, PET, CAT, SPECT and MRI. In certain embodiments the nanoconjugate can include a multi-arm polymer, imaging agent(s) and therapeutic agents(s). In another aspect, $R'''$ of Formulas 1 or 1A is an imaging agent. In yet another aspect, $R^1$-$R^4$ of Formulas 1B or 1C is an imaging agent.

In certain embodiments the nanoconjugate may include a multi-arm polymer and may further comprise one or more targeting ligand(s). Targeting ligands may include but are not limited to, antibodies, nucleic acids, aptamers, peptides, and ferromagnetic materials.

In one embodiment, the present invention includes a nanoconjugate comprising: a multi-arm nanocarrier configured for preferential intralymphatic or tumoral accumulation after percutaneous, intratumoral, intravascular, intralymphatic, nodal, peritumoral, intratissue or intraorgan administration; and one or more therapeutic agents coupled to the multi-arm nanocarrier. The nanoconjugate may have a dimension of about 5 nm to about 400 nm (e.g., about 5, 10, 15, 20, 25, 30, 40, 50, 70, 80, 100, 110, 120, 140, 160, 180, 200, 225, 250, 270, 300, 350, or 400). Also, the nanoconjugate can preferably be loaded with therapeutic agents from about 3% to about 80% w/w (e.g., about 3, 5, 10, 15, 20, 30, 35, 40, 45, 50, 55, 60, 65, 70, 75, or 80% w/w). The multi-arm polymers are typically nanocarriers having a molecular weight of about 10 kDa to about 10,000 kDa (e.g., about 10, 20, 30, 40, 50, 60, 70, 80, 90, 100, 110, 120, 130, 150, 200, 300, 400, 500, 600, 800, 1000, 1500, 2000, 3000, 4000, 5000, 6000, 7000, 8000, 9000, or 10,000 kDa). The multi-arm nanocarrier can have a charge, which may be anionic, neutral, or cationic. Preferably, the charge is anionic or neutral. The charge of the nanoconjugate can be anionic, neutral, or cationic. Preferably, the charge is anionic or neutral. More preferably, the charge when measured by zetapotential is between about −10 and −100 mV, and more preferentially between about −20 and −80 mV, and yet more preferentially between about −30 and −50 mV.

The therapeutic agents can include chemotherapeutics, which may be categorized by their mechanism of action into, for example, following groups: anti-metabolites/anti-cancer agents, such as JS-K analogs ($O^2$-(2,4-dinitrophenyl) 1-{[4-(2-(2-hydroxyethoxy))ethyl]piperazin-1-yl}diazen-1-ium-1,2-diolate (NO1) and $O^2$-(2,4-dinitrophenyl) 1-[[4-(2-hydroxy)ethyl]-3-methylpiperazin-1-yl]diazen-1-ium-1,2-diolate (NO2), pyrimidine analogs (5-fluorouracil, floxuridine, capecitabine, gemcitabine, and cytarabine) and purine analogs, folate antagonists and related inhibitors (mercaptopurine, thioguanine, pentostatin, and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones, navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, mechlorethamine, mitomycin, mitoxantrone, nitrosourea, paclitaxel, plicamycin, procarbazine, teniposide, triethylenethiophosphoramide, and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts, and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; HSP90 inhibitors, geldanamycin, antisecretory agents (brefeldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; chromatin disruptors; and combinations thereof.

Chemotherapeutics can include anti-bacterials (aminoglycosides, ansamycins, carbacephem, carbapenems, cephalosporins, glycopeptides, lincosamides, lipopeptides, macrolides, monobactams, nitrofurans, penicillins, polypeptides, quinolones, sulfonamides, tetracyclines, levofloxacin, ciprofloxacin), anti-inflammatories (NSAIDS), anti-mycobacteria agents, anti-virals, anti-fungals (imidazoles, triazoles, thiazoles, allyamines, echinocandins, amphotericin B, nystatin, bifonazole, butoconazole, clotrimazole, econazole, fenticonazole, isoconazole, ketoconazole, miconazole, omoconazole, oxiconazole, sertaconazole, sulconazole, tioconazole, Albaconazole, Fluconazole, Isavuconazole, Itraconazole, Posaconazole, Ravuconazole, Terconazole, Voriconazole, abafungin, amorolfine, butenafine, naftifine, terbinafine, anidulafungin, caspofungin, micafungin, polygodial), anti-virals, vaccines. In one aspect, the chemotherapeutic agents are selected from cisplatin, other platinum chemotherapeutic drugs, melphalan, withaferin A, mytomycin C, doxorubicin, epirubicin, docetaxel, daunorubicin, combinations thereof, and the like. Most preferred combinations involve nanoconjugates of JS-K analogs, cisplatin, doxorubicin, and/or geldanamycin. For example, the combination may comprise (1) multi-arm star-cisplatin+multi-arm star-NO-prodrug; (2) multi-arm star-doxorubicin+multi-arm star-NO-prodrug; or (4) multi-arm star-cisplatin+multi-arm star-doxorubicin+multi-arm star-NO-prodrug.

In one aspect, $R^m$ of Formula 1 or 1A is a therapeutic agent. In another aspect, $R^1$-$R^4$ of Formulas 1B or 1C is a therapeutic agent.

In another aspect, $R^m$ of Formulas 1 or 1A is selected from the group consisting of JS-K or its analogs, cisplatin, doxorubicin, geldanamycin, an NO prodrug, or combinations thereof. In still another aspect, $R^1$-$R^4$ of Formulas 1B or 1C is selected from the group consisting of JS-K or its analogs, cisplatin, doxorubicin, geldanamycin, an NO prodrug, or combinations thereof.

In another aspect, $R^m$ of Formulas 1 or 1A is an oxaliplatin derivative. Oxaliplatin may be chemically modified using two equivalents of a linker molecule, fmoc-3-amino-4-methoxybenzoic acid.

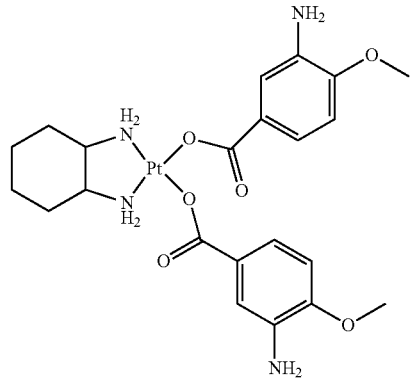

The oxaliplatin derivative provides two $NH_2$ groups for direct conjugation to the carboxylate of the linker, such as of the D-glucuronic acid of a hyaluronic acid linker using EDC chemistry. The resulting conjugate bears a stable amide bound, which liberates the free platinum chemotherapeutic in a sustained fashion. Other chemical groups besides the substituted benzoic acid could be used after the ester to increase the electron density and stabilize the ester from hydrolysis. These include more substituted benzoic acids that include electron donating groups. Other ester-linked drugs could be substituted for the oxaliplatin, such as taxanes, rapamycin, camtothecin, and other drugs containing a hydroxyl group.

In one embodiment, the present invention includes a nanoconjugate comprising: a multi-arm nanocarrier configured for preferential intralymphatic or tumoral accumulation after percutaneous, intratumoral, intravascular, intralymphatic, nodal, peritumoral, intratissue or intraorgan administration; and a one or more imaging agents coupled to the nanoconjugate. The imaging agent may be categorized by the method of imaging that the agent is commonly used with, for example MRI contrast agents (iron oxide and its chelates, gadolinium, manganese, and other paramagnetic and superparamagnetic agents and their chelates), SPECT and CAT ($^{99m}$Tc, $^{123}$I, $^{125}$I, $^{131}$I $^{111}$In, and additional radioisotopes, gamma emitters, and their chelates and conjugates), X-ray (barium and its salts, other x-ray absorbing elements and molecules), ultrasound (perfluorocarbon gases, and other bubbles or bubble forming substances), photoacoustics (organic dyes, quantum dots, gold nanoshells, gold nanorods, gold nanoparticle, carbon nanodiamonds, and other substances with high optical absorbance in the near infrared wavelengths), and fluorescence (organic dyes, organic fluorophores carbon nanodiamonds, quantum dots, and other substances which radiate energy after absorption of a different wavelength of energy, where the excitation wavelength is usually in the visible or near infrared wavelengths and the emission is usually in the near infrared wavelengths). In another aspect of this embodiment, the nanoconjugate may include a plurality of imaging agents. For example, the combination may nanoconjugate may comprise a star polymer nanocarrier+IR-820+gadolinium; or star polymer+$^{123}$I+gadolinium.

For combination therapy or coadministration therapy, at least two active compounds in effective amounts are used to treat cancer as otherwise described herein at the same time. Although the combination therapy or coadministration preferably includes the administration of two active compounds to the patient at the same time, it is not necessary that the compounds be administered to the patient at the same time, although effective amounts of the individual compounds will be present in the patient at the same time. Further, the combination therapy may include nanoconjugate compositions containing one or more of the chemotherapeutic agents (e.g., multi-arm nanocarriers coupled NO-prodrug and multi-arm nanocarriers coupled cisplatin mixed together). The multi-arm nanocarriers forming the nanoconjugate compositions may be coupled to one or more chemotherapeutic agents (e.g., multi-arm nanocarriers coupled to both NO-prodrug and cisplatin or multi-arm nanocarriers coupled to NO-prodrug, cisplatin, and doxorubicin).

In one embodiment, compositions contain between about 10% and 100% of the maximum tolerated dose of the chemotherapeutic agent(s). The chemotherapeutic agents are preferably selected from the group consisting of NO-prodrug, platinums, anthracyclines, Hsp90 inhibitors, taxanes, and HDAC inhibitors, although various combinations of the chemotherapeutic agents described herein are contemplated. In one aspect, the nanoconjugate compositions comprise about 10% to 100% (e.g., about 10, 15, 20, 25, 30, 35, 40, 45, 50, 55, 60, 65, 70, 75, 80, 85, 90, 95, or 100%) of the maximum tolerated dose of NO-prodrug. In one aspect, the nanoconjugate compositions comprise about 10% to 100% (e.g., about 10, 15, 20, 25, 30, 35, 40, 45, 50, 55, 60, 65, 70, 75, 80, 85, 90, 95, or 100%) of the maximum tolerated dose of cisplatin. In another aspect, the nanoconjugate compositions comprise about 10% to 100% (e.g., about 10, 15, 20, 25, 30, 35, 40, 45, 50, 55, 60, 65, 70, 75, 80, 85, 90, 95, or 100%) of the maximum tolerated dose of NO-prodrug and comprise about 10% to 100% (e.g., about 10, 15, 20, 25, 30, 35, 40, 45, 50, 55, 60, 65, 70, 75, 80, 85, 90, 95, or 100%) of the maximum tolerated dose of cisplatin.

In one embodiment, compounds of the present invention comprise chemotherapeutic or imaging agents coupled to the multi-arm nanocarrier via a degradable linker. Exemplary degradable linkers include disulfide linkers, acid labile linkers, peptidase labile linkers, and esterase labile linkers. For example, the degradable linker is acid-labile or degradable by enzymes. In one aspect of this embodiment, the linker may be degraded in the presence of enzymes (e.g., PSMA or matrix metalloproteinases), proteins, or chemicals (for example peroxides) present at higher concentrations in tumor or lymphatic tissues than some other tissues. In another aspect of this embodiment, the linker may be degraded by light from an external source, for example a laser light that is between about 500 and about 1200 nm (e.g., 500, 550, 600, 650, 700, 750, 800, 850, 900, 950, 1000, 1050, 1100, 1150, or 1200 nm). In another aspect of this embodiment, the linker may be degraded when the tissue is at a higher temperature than commonly found in the body, for example with focused heating from ultrasound, magnetic sources, laser or infrared light irradiation, or an applied heating source (e.g., heating pad, perfusions of heated fluids, heated bath).

In one embodiment, the therapeutic agent or imaging agent and the multi-arm nanocarrier (or nanoparticle) are coupled by charge-charge interactions, ionic bonds, covalent bonds, hydrogen bonding, hydrophobic forces, or a combination of a plurality of forces herein.

In one embodiment, the chemotherapeutic agents are not biologically active until triggered, for example by enzymes, proteins, or chemicals (for example peroxides) present at higher concentrations in the tumor or lymphatic tissues than some other tissues; by laser irradiation or infrared light irradiation; by ultrasound; or by heating of the tissue to a higher temperature than the nominal body temperature, for example heating to between 38 and 46 C (for example, 38, 39, 40, 41, 42, 43, 44, 45, or 46° C.). In another aspect of this embodiment, the heating is transient and of a temperature higher than those normal founding in the body, for transient heating for less than 10 s (e.g., 10, 5, 1 s, 100 ms, 10 ms, 1 ms, 0.1 ms, 0.001 ms) and a temperature between 40 and 90 C (e.g., 40, 50, 60, 70, 80 or 90° C.).

In one embodiment, the nanoconjugate includes a conjugated targeting ligand. The targeting ligand can comprise of one or more of antibodies, nucleic acids and derivatives, peptides and derivatives, proteins, and ferromagnetic materials. For example, nucleic acid derivatives may include aptamers (e.g., PSMA or HER2 aptamer). Antibodies may include polyclonal and monoclonal antibodies (e.g., anti-EGF receptor, anti-HER2). Proteins may include EGF or epidermal growth factor, or matrix metalloproteinases.

The multi-arm nanocarrier can be a polymer that includes a core and a plurality of arms. The arms can be connected to the core by a linker. Preferred linker may have one or more of an ester, hydrazole, or ketal functionality. Exemplary nanocarriers having four arms are illustrated in the examples. However, nanocarriers having 2, 3, 4, 5, 6, 7, or 8 arms are with the scope of the present invention.

The arms are coupled to one or more linkers L′′′. Attachment of the L′′′ to the arms and/or attachment of L′′′ to the R′′′ may be obtained using a bioorthogonal coupling reactions, which may include, but are not limited to the chemistry found in Native Chemical Ligation (NCL) and Expressed Protein Ligation (EPL), carbonyl ligations, Diels-Alder reactions, Pd- and Rh-catalyzed ligations, decarboxylative condensations, thioacid/azide ligations, maleimide/thiol pairs, aziridine ligations, the Staudinger ligation, and the Sharpless-Huisgen cycloaddition. These reactions are often cited as examples of "click chemistry," a term used in the art to refer to chemical reactions that are specific, high yielding, and tolerant of functional groups.

In another aspect, $L^m$ of Formulas 1 or 1A are each independently a degradable linker having one or more of an ester, hydrazole, or ketal functionality. In still another aspect, $L^1$-$L^4$ of Formulas 1B and 1C are each independently a degradable linker having one or more of an ester, hydrazole, or ketal functionality.

The arms of the multi-arm nanocarriers can comprise a repeating subunit wherein the repeating subunits are connected using a polymerization reaction (e.g., MADIX/RAFT polymerization, ring opening polymerization) that results in a linker between the subunits (e.g., a vinyl, amide, ester, alkyl, hydrazole, or ketal, any one of which may be substituted or unsubstituted). Thus, in one aspect, at least one linker is a polymerization reaction product from one or more of a vinyl, amide, ester, alkyl, hydrazole, or ketal, which is substituted or unsubstituted.

In another aspect, subunits of the linker may comprise a substantially neutral, anionic or cationic chemical species. In another aspect, linker may include subunits which comprise one or more a sugars or carbohydrates. The sugars may include simple or complex sugars such as glucose, galactose, sucrose, lactose, glucuronic acid, and N-acetylglucoamine, or homogenous or heterogeneous disaccharides or higher order polysugars. In another aspect, the linker may include subunits comprising one or more amino acids, peptides, polyesters, polyvinyls, polyanhydrides, polylactones, or other biodegradable material and biocompatible materials. In one aspect, linker may have heterogeneous subunits or contain a plurality of subunits described herein. In another aspect, the linker may include homogeneous subunits. In another embodiment, the subunits may comprise repeating subunits, which may include sugars, peptides, or amino acids. The sugars may include derivatives of sugars, such as those formed by the addition of carboxylic acids, aldehydes, amides, ethers, esters, ketals, hydrazones or conjugates to those sugars. For example, the sugar can be a galactose which includes one or more carboxylic acids, which can be formed by addition of succinic acid to the galactose.

In still another aspect, the linker may be comprised of hyaluronic acid or its derivatives. For example, hyaluronan may be coupled with the propargylamine using $NaCNBH_3$ as a reducing agent (e.g. at about pH 5.6 and 50° C.). Subsequently, the hyaluronan polymers may grafted to the multi-arm core modified to have an azide terminus by a "click" reaction under the catalysis of Cu(I). The hyaluronan polymer or derivative thereof preferably has a molecular weight of about 1 kDa to 300 kDa in each arm, more preferably between 3 kDa and 100 kDa, and more between 20 kDa and 80 k kDa.

In one aspect, $L^m$ of Formulas 1 or 1A are each independently include a hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, nucleic acids, polynucleotides, derivatives thereof, or combinations thereof.

In another aspect, $L^1$-$L^4$ of Formulas 1B or 1C are each independently a hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, nucleic acids, polynucleotides, derivatives thereof, or combinations thereof.

In one aspect, the present invention is directed to making the compounds of the present invention. An exemplary scheme for making the compounds of Formulas 1, 1A, 1B, 1C, and 2 is as follows:

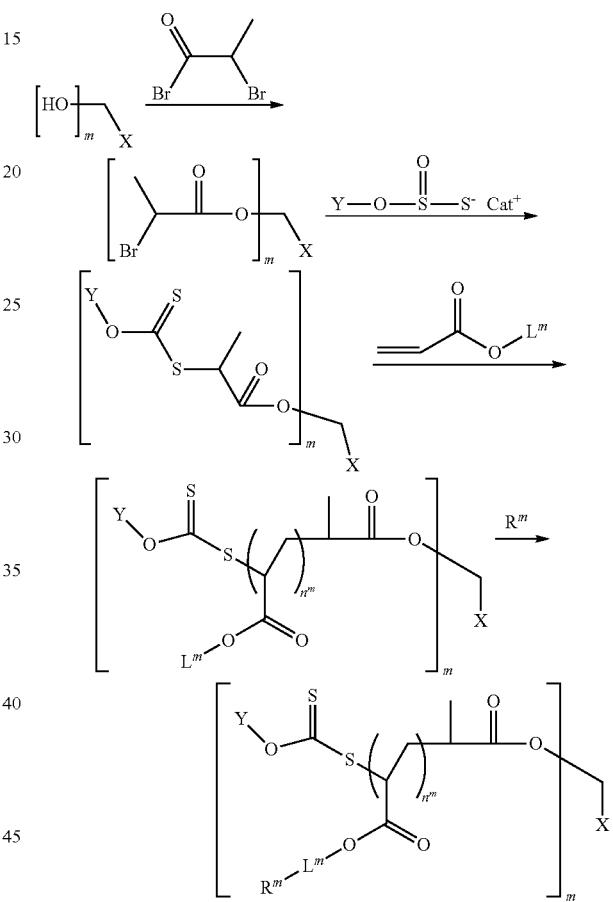

wherein: X is one of carbon (C), oxygen (O), nitrogen (N), phosphorous (P), or sulfur (S); m is 2, 3, 4, 5, 6, 7, or 8; Y is alkyl (preferably a $C_1$-$C_6$ alkyl, e.g. methyl, ethyl, propyl, etc); and $Cat^+$ is a cation (preferably $Na^+$, $Li^+$, $K^+$); $L^m$ are each independently a bond or a linker; $R^m$ are each independently a therapeutic agent or imaging agent; and $n^m$ are each independently an integer; and wherein -$L^m$-$R^m$ together may be hydrogen (H).

In one embodiment, the present invention includes a method for treating and/or inhibiting cancer. Such a method can include percutaneously, peritumorally or intratumorally administering a composition having a multi-arm or star polymer carrier, and a nanoconjugate configured for preferential intralymphatic accumulation after subcutaneous, peritumoral or intratumoral administration. The nanoconjugate can be any embodiment as described herein. Further, the composition may be co-administered with one or more other active agents, such as the chemotherapeutics described herein.

In another embodiment, the present invention includes an imaging method. Multi-arm or star polymers having an imaging agent conjugated thereto may be administered to a subject in need of imaging or diagnostic testing.

In one embodiment, the multi-arm nanocarrier has between 2 and 8 arms (e.g., 2, 3, 4, 5, 6, 7, or 8). In another aspect of the embodiment, the arms can have subarms that include repeating subunits.

In one embodiment, the present invention includes a method for treating and/or inhibition of infection by a foreign agent, for example including anti-bacterials, anti-virals, anti-fungals, and vaccines. In certain aspects of the embodiment, the nanoconjugate may function as an adjuvant.

In one embodiment, the nanoparticle is highly water soluble, in excess of 10 mg/mL, more preferred in excess of 20 mg/mL, and more preferred in excess of 30 mg/mL and even more preferred in excess of 50 mg/mL, and even more preferred in excess of 70 mg/mL and even more preferred in excess of 200 mg/mL and even more preferred in excess of 300 mg/mL.

In one embodiment, the nanoconjugate between the therapeutic agent and nanoparticle is substantially more soluble than the therapeutic agent without the nanoparticle in an aqueous milieu, wherein the aqueous milieu contains more water than organic solvents. In one embodiment the nanoconjugate which includes a star polymer is more soluble than a conjugate which includes a multi-arm nanocarrier formed from a substantial linear polymer, where in the substantially linear polymer can have less than 3 arms (e.g., hyaluronan, dextran, PEG).

In one embodiment, the nanoconjugate is substantially less viscous than a nanoconjugate formed using a polymer that is substantially linear. The less viscous nanoconjugate can be more easily administered to the body through a delivery device, such as a needle, catheter, or other devices used to place drugs into the body via the injection routes described herein for preferential delivery to tumors, lymphatics, and their surrounding tissues or tissues with enhanced potential for tumor metastasis or spread. In one aspect of the embodiment, the nanoconjugate solution, which includes sufficient drug for safe administration or reasonable therapeutic effect after one or more injections into the body over a treatment session, has a viscosity of less than 2000 cp, and more preferable a lower viscosity (e.g., less than 1500, 1000, 700, 500, 400, 300, 200, 150, 100, 75, 50, or even more preferable less than 25 cp). Lower viscosities can enable more concentrated solutions of the nanoconjugate, which can allow smaller injection volumes into patients, which can reduce pain and tissue damage to patients and improve their therapy experience and therapy outcome. Low viscosity solutions may be require less effort on the part of medical provider to administer or allow the use of a smaller delivery or administration device that would improve the therapy of the patient.

EXAMPLES

Unless noted otherwise, all reagents and solvents were purchased from Sigma Aldrich and used without further purification. Milli-Q water was used in all experiments. $^1$H-NMR (400 MH$_z$) and $^{13}$C-NMR (100 MH$_z$) spectra were collected on a Bruker DRX 400 spectrometer using compounds dissolved in CDCl$_3$, MeOD or D$_2$O. Chemical shifts were referenced to 87.28 and 77.0 ppm for $^1$H-NMR and $^{13}$C-NMR spectra, respectively. High-resolution mass spectrometry (HRMS) data were generated after flow injection analysis (FIA) manually matching peaks on an Applied Biosystems Mariner TOF spectrometer with a turbo-ion spray source. The Griess Reagent kit was purchased from Promega Corporation (Madison, Wis.). Cell culture media were purchased from Fisher Scientific (Pittsburgh, Pa.). The MDA-1986 cell line was kindly provided by Mark Cohen (University of Kansas Medical Center, Kansas City, Kans.), while MCF-7, MDA-MB-231, B16F10 and A2058 cells were obtained from the American Tissue Culture Collection (ATCC, Manassas, Va.). Animal procedures were approved by the University of Kansas Institutional Animal Care and Use Committee. Balb/C and Nu/Nu mice were purchased from Charles River Laboratories (Wilmington, Mass.).

Example 1

Synthesis of MADIX/RAFT Agent

Figure 2:
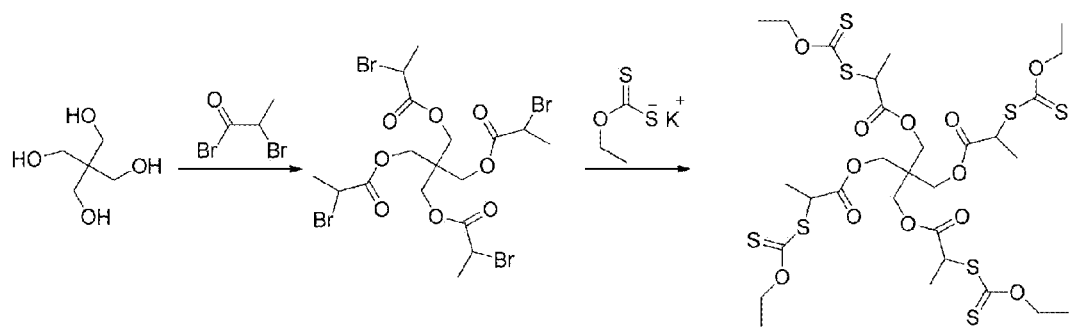
FIG. 2 includes a scheme of the synthesis of MADIX/RAFT agent.

The MADIX/RAFT agent was synthesized and reported in FIG. 2. The core starting material, pentaerythritol, was esterified with 2-bromopropionyl bromide and O-ethylxanthic acid (potassium salt), successively, to form a four-arm sulfur compound that was used as the MADIX/RAFT initiator agent.

For example, pentaerithol (1.36 g, 10 mmol) was dissolved in 25 mL of dry chloroform and 2.5 mL of pyridine and cooled to 0° C. The 2-bromo propionyl bromide (10.01 g, 45 mmol) was added dropwise, and the reaction proceeded at ambient temperature (ca. 23° C.) for 48 hours. The mixture then was neutralized with aqueous HCl (10 wt %). Then the organic phases were washed with water, sodium bicarbonate solution (5%) and then brine, followed by drying with sodium sulfate. The solvent was evaporated under reduced pressure, which yielded the desired compound. The molecular structure was verified by $^1$H-NMR and compared with the reported data.

For example, a solution of the intermediate compound (2.028 g, 3.0 mmol) in chloroform (45 mL) was treated with a 10-fold excess of O-ethylxanthic acid, potassium salt (5.01 g, 30 mmol). The mixture was stirred at ambient temperature for 3 days, and the resulting suspension was filtered and washed with chloroform. Evaporation of the solvent followed by purification through a flash column on silica gel using 3:7 ethyl acetate:hexanes as eluents yielded the desired compound, and the molecular structure was verified by $^1$H-NMR and compared with the reported data.

Example 2

Synthesis of 4-Arm Tert-Butyl Acrylate Star Polymer

Figure 3:
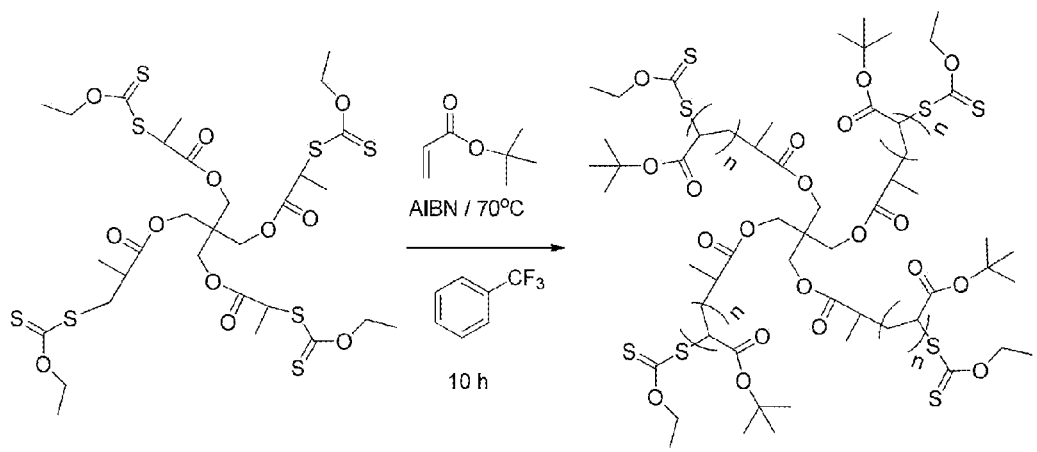
FIG. 3 includes a scheme of the synthesis of multi-arm tert-butyl acrylate star polymers.

The multi-arm tert-butyl acrylate star polymer was synthesized as reported in FIG. 3. For example, the tert-butyl acrylate (2.50 g, 19.5 mmol) was treated with basic alumina and 10 mL of dry α,α,α-trifluorotoluene in a 50-mL round bottom flask. The MADIX/RAFT agent from Example 1 (27 mg, 3.25×10$^{-2}$ mmol) was added to the solution, followed by the addition of azobisisobutyronitrile (AIBN) (0.53 mg, 3.25× 10$^{-3}$ mmol), and the reaction flask was placed on ice and purged with argon for 30 minutes. The flask then was transferred to a thermostatic oil bath at 70° C. for ca. 12 hours. The mixture was cooled in an ice bath and poured into cold diethyl ether to obtain the precipitate followed by concentration under reduced pressure (FIG. 3). The molecular structure and molecular weight of the resulting polymer were determined by $^1$H-NMR and SEC, respectively (see Example 7). Poly (tert-butyl acrylate) star polymer, $^1$H-NMR (CDCl$_3$, 400 MHz): δ=4.65 (q, 8H), 4.25 (q, 4H), 4.03 (q, 8H), 2.25 (brs), 1.86 (brs), 1.65-1.27 (brs, overlap).

The MADIX/RAFT polymerization approach is of special interest to polymer and drug delivery scientists compared to other synthetic strategies involving free radical reactions, including NMP, ATRP, and RAFT, as a wide range of potential monomers could be readily utilized to generate well-controlled polymeric architectures. The polymerization resulted in 90% conversion of the monomers after a reaction duration of approximately 14 hours. Reaction byproducts started to form if the reaction was allowed to proceed for longer than 20 hours.

Example 3

Synthesis of Multi-Arm Acrylic Acid Star Polymers

Figure 4:
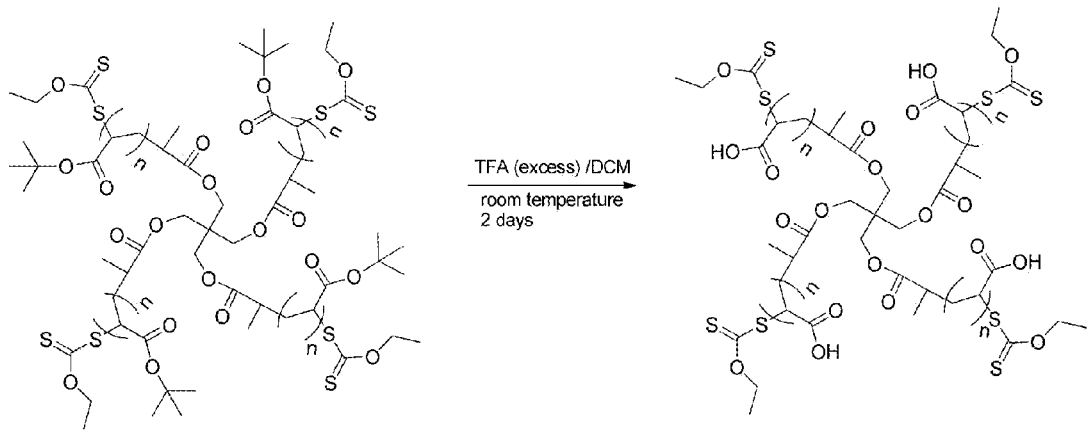
FIG. 4 includes a scheme of the synthesis of multi-arm acrylic acid star polymer from tert-butyl acrylate star polymer.

The multi-arm acrylic acid star polymer was synthesized and reported in FIG. 4. For example, the tert-butyl acrylate star polymer from Example 2 (2.50 g, 19.5 mmol) was dissolved in 200 mL of dichloromethane, and 75 mL of trifluoroacetic acid (TFA, 975 mmol) was then added. The mixture was stirred vigorously until the generation of white precipitate ceased. The precipitate was filtered and washed with dichloromethane and diethyl ether, and then dried under reduced pressure overnight. Treatment of the poly(tert-butyl acrylate) star polymers of different molecular weights with TFA acid in dichloromethane yielded the corresponding acid star polymers. The molecular structures and weights of the resulting polymers (FIG. 4) were determined by $^1$H-NMR and SEC (see Example 7), respectively. $^1$H-NMR (CDCl$_3$, 400 MHz): $^1$H-NMR (CDCl$_3$, 400 MHz): $\delta$=4.66 (q, 8H), 4.30 (q, 4H), 4.14 (q, 8H), 2.25 (brs), 1.86 (brs), 1.65-1.27 (brs, overlap), 1.30 (t, 12H). In this example, n may range from 2 to 500, but is typically between about 2 and 30.

Example 4

Synthesis of Poly(Acrylic Acid) Star Polymer-Cisplatin Conjugates

Figure 5:
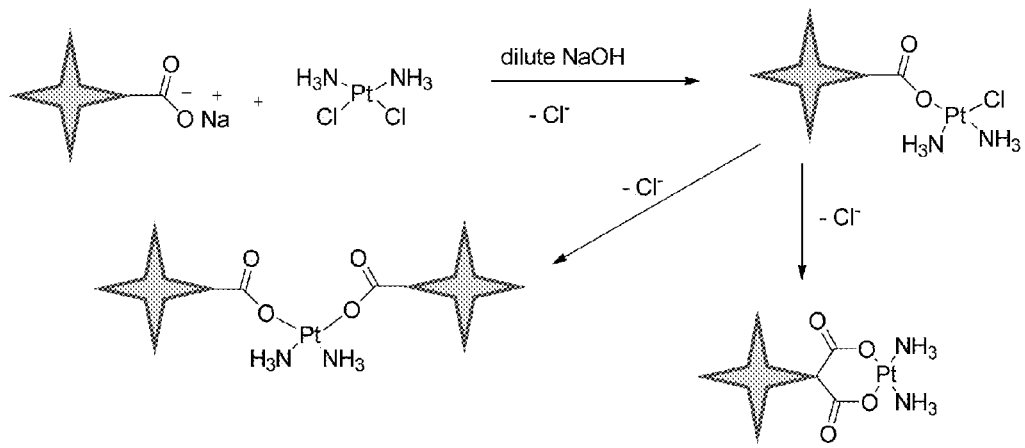
FIG. 5 includes a scheme of the synthesis of poly(acrylic acid) star polymer-cisplatin conjugates.

The poly(acrylic acid) star polymer-cisplatin conjugates (acid-Pt) were synthesized and reported in FIG. 5. For example, poly(acrylic acid) star polymer (50 mg) was dissolved in 25 mL of dd H$_2$O in a 50-mL round bottom flask. The pH of the solution was adjusted to 10 using 1-M NaOH solution and 25 mg of cisplatin was added. The solution was stirred under argon protection at ambient temperature for 36 hours. The solution then was dialyzed (10-kDa MWCO tubing, Pierce, Rockford, Ill.) against distilled water at 4° C. for 2 days with water changes every 6 hours to remove the unbound cisplatin. After dialysis the resulting polymer was concentrated by rotary evaporation to obtain the desired multi-arm poly(acrylic acid) star polymer-cisplatin conjugates (FIG. 5).

Example 5

Figure 6:
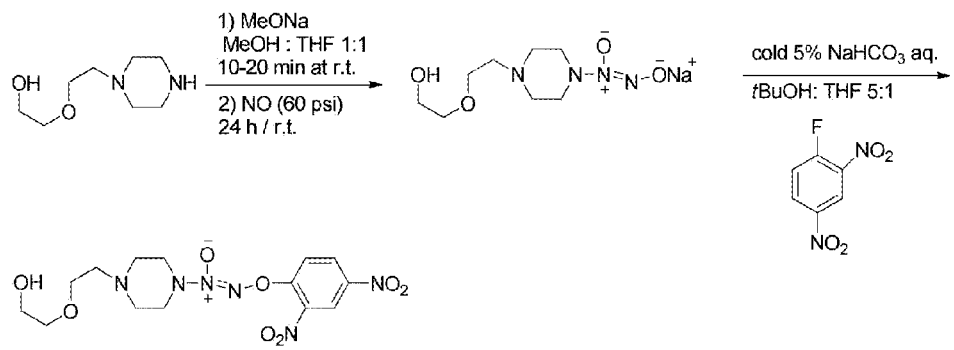
FIG. 6 includes a scheme of the synthesis of $O^2$-(2,4-Dinitrophenyl) 1-{[4-(2-(2-hydroxyethoxy))ethyl]piperazin-1-yl}diazen-1-ium-1,2-diolate.

Synthesis of a nitric oxide-donating prodrug NO1, $O^2$-(2,4-Dinitrophenyl) 1-{[4-(2-(2-hydroxyethoxy)) ethyl]piperazin-1-yl}diazen-1-ium-1,2-diolate The nitric oxide prodrug was synthesized and reported in FIG. 6. For example, the 1-[2-(2-hydroxyethoxy)ethyl]piperazine (5.0 g, 27.3 mmol) was dissolved in 2 mL of methanol and treated with 25% w/v methanolic sodium methoxide (6.2 mL) and ether (20 mL). The resulting solution was charged with NO at 60 psi and stirred at ambient temperature for 24 hours, leading to the formation of a white precipitate. The white solid was filtered, washed with ether, and dried under reduced pressure to afford the sodium 1-[2-(2-hydroxyethoxy)ethyl]homopiperazin-1-yl]diazen-1-ium-1,2-diolate. Subsequently, the white solid was dissolved in 60 mL of 5% w/v ice cold sodium bicarbonate solution. The solution was treated with 1-fluoro-2,4-dinitrobenzene (4.67 g, 25.1 mmol) pre-dissolved in a mixture of 30 mL of t-BuOH and 5 mL of THF. A yellow precipitate formed immediately and was purified by silica flash chromatography (CHCl$_3$: EtOAc=9:1) to afford the desired compound. The molecular structure was verified by $^1$H-NMR and mass spectrometry.

$^1$H-NMR (CDCl$_3$, 400 MHz): $\delta$=1.69 (brs, 1H), 2.70 (t, J=5.3 Hz, 2H), 2.80 (t, J=5.1 Hz, 4H), 3.63-3.66 (m, 2H), 3.69-3.75 (m, 8H), 7.68 (d, J=9.3 Hz, 1H). 8.47 (dd, J=9.2, 2.7 Hz, 1H), 8.90 (d, J=2.7 Hz, 1H); $^{13}$C-NMR (CDCl$_3$, 100 MHz): $\delta$=50.3, 51.5, 57.0, 61.9, 68.0, 72.3, 117.6, 122.2, 129.1, 137.2, 142.3, 153.9. HRMS (ESI) Calculated for $C_{14}H_{21}N_6O_8$ (M+H)$^+$: 401.1421; Found: 401.1413.

Example 6

Synthesis of Poly(Acrylic Acid) Star Polymer-Nitric Oxide Prodrug Conjugates

Figure 7:
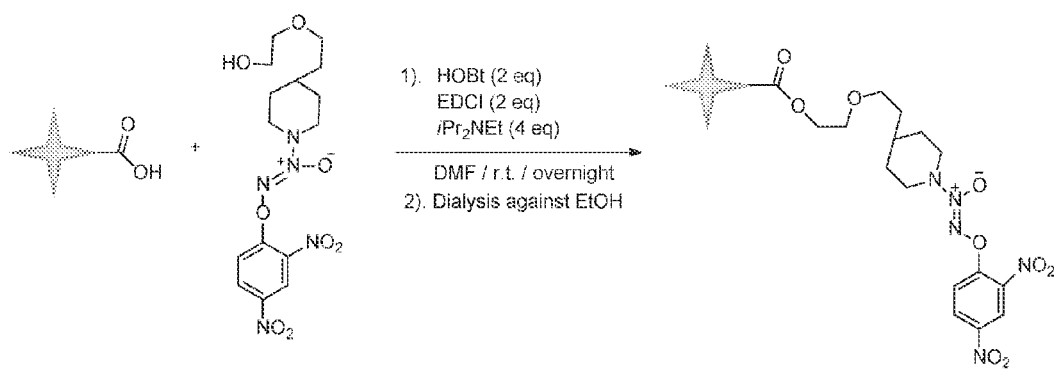
FIG. 7 includes a scheme of the synthesis of poly(acrylic acid) star polymer-nitric oxide prodrug conjugates.

The poly(acrylic acid) star polymer-nitric oxide prodrug conjugates were synthesized and reported in FIG. 7. For example, the poly(acrylic acid) star polymer (50 mg) was dissolved in 25 mL of ice cold DMF: dd H$_2$O (25:1 v/v) mixture in a 50-mL round bottom flask (FIG. 7), and EDCI·HCl (1.5 eq) and HOBt.H$_2$O (1.5 eq) were added to the solution. After 5 minutes, NO1 from Example 5 (1.0 eq) was added to the solution. The reaction proceeded under argon at 0° C. for 30 minutes, followed by ambient temperature overnight in the dark. The resulting acid-NO conjugate was dialyzed using 10,000 MWCO tubing against a mixture of dd H$_2$O:ethanol (1:1 v/v) at ambient temperature for 12 hours, followed by ethanol for another 12 hours. The desired acid-NO conjugates were obtained after the evaporation of the solvent under reduced pressure. The molecular structure was verified by $^1$H-NMR. $^1$H-NMR (CDCl$_3$, 400 MHz): $\delta$=8.90 (d, J=8.4 Hz, 1H), 8.57 (dd, J=8.4 Hz, 1H), 7.68 (d, J=13.2 Hz, 1H), 4.66 (q, 8H), 4.30 (q, 4H), 4.14 (q, 8H), 3.73 (m, 8H), 3.65 (m, 2H), 2.79 (m 4H), 2.70 (m, 2H), 2.73 (brs), 1.81-1.48 (brs, overlap).

The acid star polymer and its corresponding polymer-chemotherapeutic conjugates, including acid star polymer-nitric oxide prodrug conjugate (Example 6) and acid star polymer-cisplatin conjugate (Example 4) were successfully synthesized. The acid star polymers were soluble in water, methanol, DMF and DMSO.

Example 7

Characterization of Acid Star Polymer by Size Exclusion Chromatography

The molecular weights and PDI of the multi-arm tert-butyl acrylate star polymers were determined using EZStart 7.4 software and a Shimadzu 2010CHT system equipped with a RID-10A refractive index detector and a TSK gel multipore Hx-M 7.8×30 cm column using 10-mM LiCl in DMF (0.8 mL/min) as the mobile phase. The calibration curve was generated using polystyrene standards ranging from 1,180 to 339,500 g/mol. After deprotection, the resulting multi-arm poly(acrylic acid) star polymer was highly soluble in methanol, water, DMF, and DMSO. The molecular weights of the multi-arm poly(acrylic acid) star polymers were determined by SEC using polyethylene glycol (PEG) standards ranging from 3,070 to 66,100 g/mol (Scientific Polymer Products, Inc) (FIG. 8, Table 1).

Figure 8:
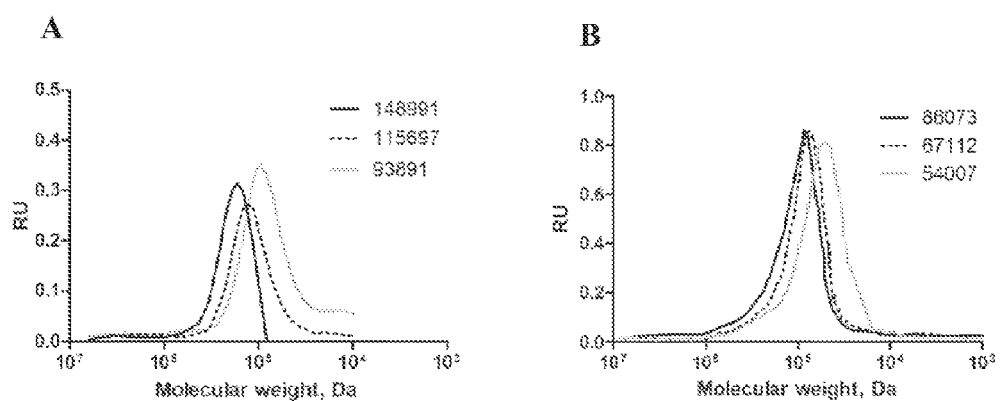
FIGS. 8A-8B include size exclusion chromatography (SEC) traces of poly(tert-butyl acrylate) star polymers and poly(acrylic acid) star polymers.

The molecular weights of the poly(tert-butyl acrylate) star polymers and their corresponding acid star polymers were determined by SEC using polystyrene and polyethylene glycol (PEG) as standards, respectively (FIG. 8). The PDIs of poly(tert-butyl acrylate) star polymer and acid star polymer with increasing molecular weights were calculated and reported in Table 1. The PDI was in part due to using linear PEGs and polystyrenes as molecular weight standards, since standards with similar architecture were not available. Also, the highly charged nature of the polymers may have led to some interactions with the column stationary phase.

TABLE 1

| Poly(tert-butyl acrylate) star polymers* | | | Poly(acrylic Acid) star polymers ‡ | | |
|---|---|---|---|---|---|
| $M_{w, SEC}$ | $M_{n, SEC}$ | PDI | $M_{w, SEC}$ | $M_{n, SEC}$ | PDI |
| 148,991 | 130,122 | 1.14 | 86,073 | 72,321 | 1.19 |
| 115,697 | 97,107 | 1.19 | 67,112 | 55,927 | 1.20 |
| 83,788 | 71,209 | 1.16 | 54,007 | 39,992 | 1.31 |

Table 1 shows the weight average molecular weights ($M_w$), number average molecular weights ($M_n$), and polydispersity indices (PDI) of poly(tert-butyl acrylate) star polymers* and poly(acrylic Acid) star polymers ‡.

Example 8

Determination of Drug Conjugation in Acid Star Polymer Conjugates

Figure 9:
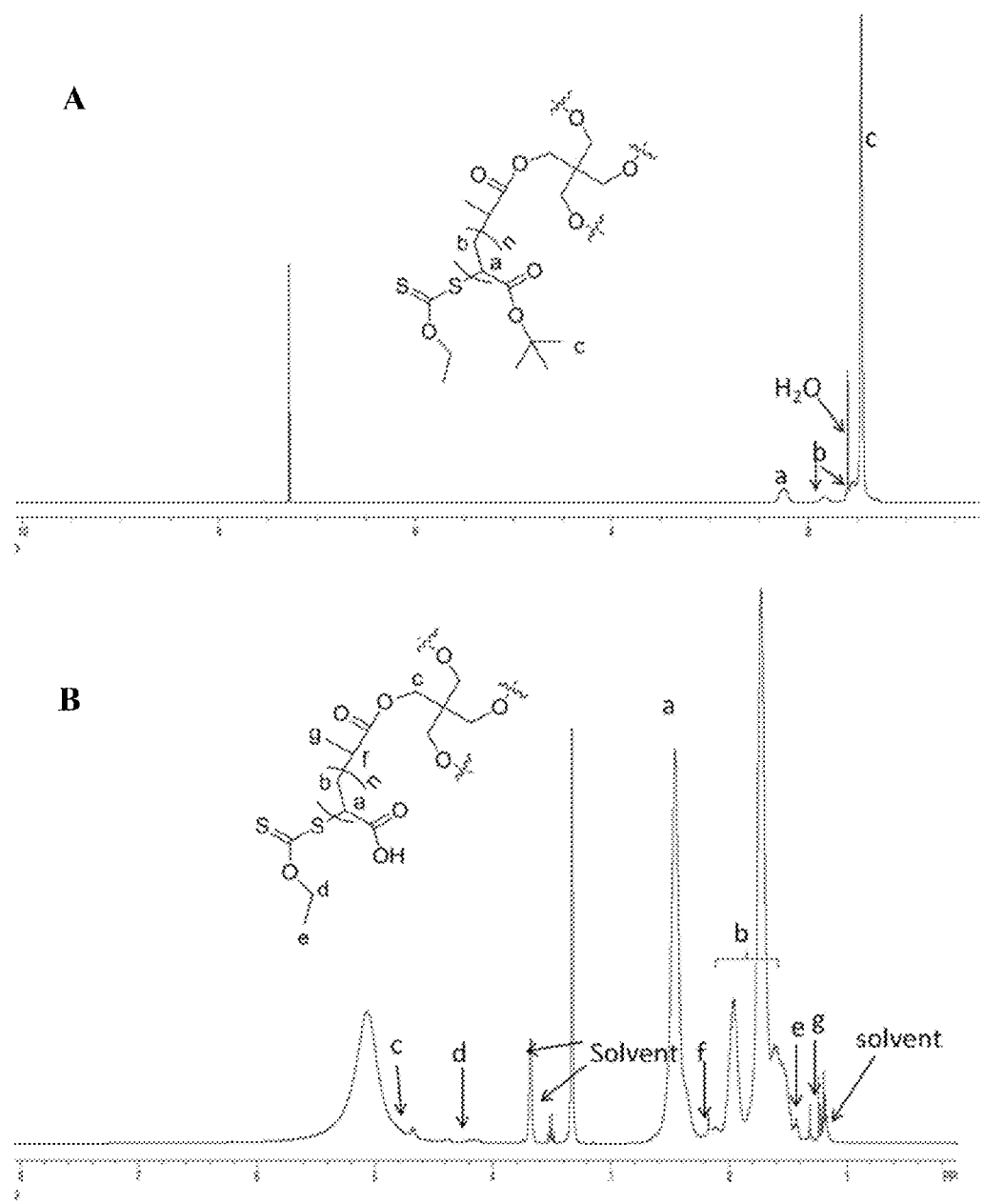
FIGS. 9A-9B include $^1$H-NMR spectra of poly(tert-butyl acrylate) star polymer (panel A, solvent: $CDCl_3$), and poly(acrylic acid) star polymer (panel B, solvent: MeOD).

The substitution degree of the NO1 prodrug on the acid-NO1 conjugate was determined by $^1$H-NMR based on the ratio of the aromatic protons of the NO1 prodrug to the methylene protons of the polymer core (FIG. 9). NMR was used for the characterization of both the polymer. The loading degree of NO1 varied from about 10 to 30 percent (e.g., 12.5% wt and 25% wt of NO1 on the conjugate).

The degree of cisplatin substitution was determined by atomic absorption spectroscopy (AAS) (Varian SpectrAA GTA-110 with graphite furnace) using platinum standards ranging from 100 to 450 ppb. The furnace program was as follows: ramp from 25 to 80° C., hold 2 seconds, ramp to 120° C., hold 10 seconds, ramp to 1000° C., hold 5 seconds, ramp to 2700° C., hold 2 seconds, cool to 25° C. over 20 seconds. The graphite partition tube was cleaned every 40 samples by baking at 2800° C. for 7 seconds. Argon was used as the injection and carrier gas. The loading degree of NO1 varied from about 10 to 30 percent (e.g., 12.5% wt and 25% wt).

Example 9

Viscosity of Acid Star Polymers

Figure 10:
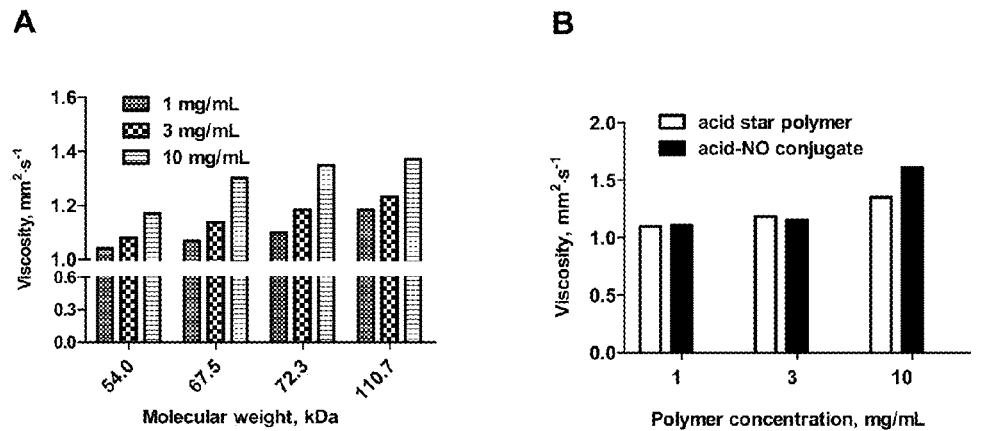
FIGS. 10A-10B include two graphs of the viscosity measurements of poly(acrylic acid) star polymers at concentrations of 1, 3, and 10 mg/mL, and star polymer nitric oxide prodrug conjugates (72.3 kDa).

The viscosity parameters of multi-arm nanocarriers and nanoconjugates were measured using a Stabinger viscometer (SVM 3000, Anton Paar, USA) and reported in FIG. 10. A series of multi-arm poly(acrylic acid) star polymer samples (MW: 54,000; 67,500; 72,300; 110,700 g/mol) were prepared by dissolving the polymers in dd $H_2O$ at three concentrations including: 1.0 mg/mL, 3.0 mg/mL and 10.0 mg/mL.

The viscosity of acid star polymers slightly increased with increases in either the molecular weight (54.0 to 110.7 kDa) or the concentration (1 to 10 mg/mL) of the polymer (FIG. 10A). The viscosity of the acid-NO conjugates was also evaluated and compared to the acid star polymer itself at three different concentrations (1, 3, 10 mg/mL). The acid star polymer selected for the drug conjugation had a molecular weight of 72.3 kD. Based on ongoing studies, star polymers with a molecular weight close to 75 kD exhibit advantageous patterns of lymphatic drainage and retention, compared to star polymers of higher or lower molecular weights, thus, the 72.3-kD star polymer drug carrier may be a potential candidate for localized drug delivery applications. It is worth noting that none of the acid star polymers tested exhibited high viscosity compared to other polymeric injectables for localized drug delivery, including hyaluronic acid, which demonstrated a 3-fold increase in viscosity relative to acid star polymers with a similar molecular weight at 10 mg/mL. Thus, these polymers are highly suited for a locally administered chemotherapeutics due to their low viscosity at high concentrations, which allows the use of small-bore needles and low injection volumes.

Example 10

In Vitro Release of Drug from Acid Star Polymers

Figure 11:
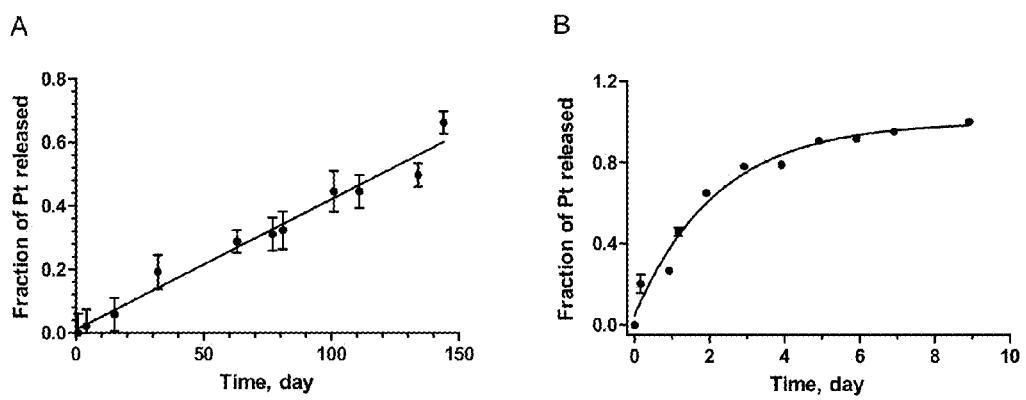
FIGS. 11A-11B include two graphs of the release kinetics of platinum from poly(acrylic acid) star polymer-cisplatin conjugates.

The in vitro release kinetics of cisplatin was determined and reported in FIG. 11 and Table 2. The acid-Pt conjugate (10 mg) was dissolved in PBS, transferred to dialysis tubing (10,000 Da MWCO), and placed in a PBS bath (pH 7.4, 37° C.) without 10% bovine serum albumin (FIG. 11A) and with 10% bovine serum (FIG. 11B) and 0.2% sodium azide. Two hundred microliter aliquots were collected from the tubing at pre-determined intervals and stored at −80° C. until analysis by AAS. The AAS produced a linear concentration curve from 10 to 450 ng/mL ($R^2$=0.9998), with a limit of detection of 5 ng/mL and a limit of quantification of 10 ng/mL (5% standard deviation).

Figure 12:
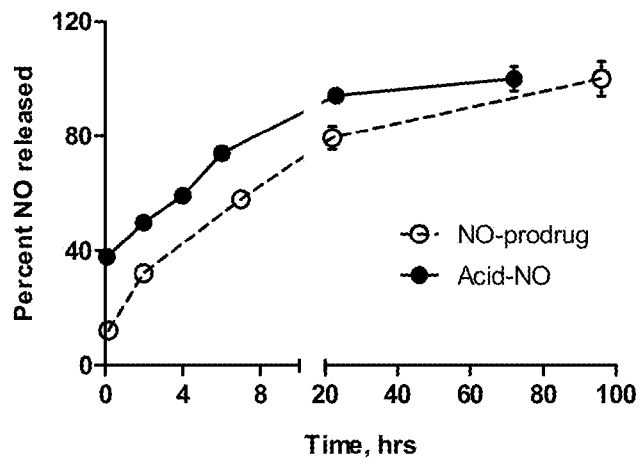
FIG. 12 includes a release study of nitric oxide from NO-prodrug and poly(acrylic acid) star polymer-NO-prodrug conjugates in cell culture media at 37° C. (N=3). The half-lives were determined be 7.4 and 5.3 hours for NO-prodrug and poly(acrylic acid) star polymer-NO-prodrug conjugates, respectively, by fitting the release data to a first order decay model using GraphPad 5 ($R^2$>0.97 for all fits).
Figure 13:
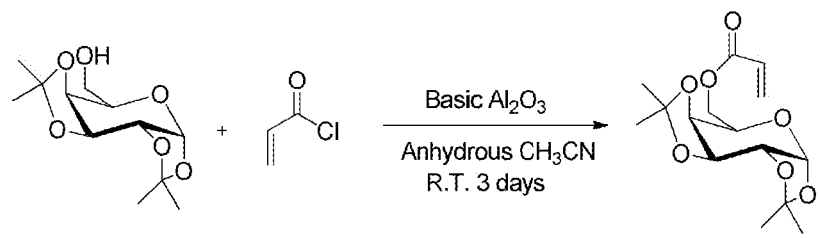
FIG. 13 includes the structure of a multi-arm sugar polymer. The multi-arm poly-(6-O-methacryloyl-D-galactose) polymers were modified with succinic anhydride, which yielded the multi-arm sugar acid star polymer.

The release half-life of nitric oxide from NO-prodrug (NO1) and acid-NO1 conjugates was determined in cell culture and reported in FIG. 12 and Table 2. MCF-7 cells were seeded in 96-well plates 24 hours prior to drug treatment (100 μL/well). On the following day, cells were treated with 20 μM of either the nitric oxide prodrug, NO1, or the multi-arm polymer based nitric oxide prodrug conjugate, acid-NO1. Fifty microliters of cell culture media were collected from each plate at 10 minutes, 2, 7, 22, 48, and 96 hours, post treatment to determine the nitrite content (N=5). The Griess reaction was performed according to the manufacturer's protocol. The absorbance was measured at 535 nm using a UV microplate reader. The nitrite concentration and the corresponding nitrite oxide levels were determined using the nitrite standard curve previously generated.

The release kinetics of cisplatin from the acid star polymer backbone was determined in PBS (pH 7.4) at 37° C. with or without 10% serum. The half-life was determined by fitting the release data to either a zero order linear regression model (release of Pt in PBS without serum) or a first order decay model (release of Pt in serum-containing PBS) using GraphPad 5 ($R^2$>0.97 for all fits). The acid-Pt conjugates demonstrated an extended shelf-life in PBS with a platinum release half-life of approximately 120 days, which is significantly more stable than other sustained delivery platforms of cisplatin, including cisplatin-incorporating polymeric micelles (release half-life: ca. 4 days), and dextran-based cisplatin conjugates (release half-life: ca. 2 days). The presence of serum expedited the drug release from the acid polymers, which is likely due to the competitive binding between the platinum and the proteins present in the serum. The conjugates were able to sustain the release of cisplatin over 9 days (95% complete) with a release half-life of approximately 36.7 hours in serum-containing PBS, suggesting satisfactory stability in plasma in vivo. If this delivery platform could be translated into the clinic, it may be utilized as an adjuvant or maintenance chemotherapy post surgery, releasing a steady concentration of platinum for an extended period of time, which may eradicate the residual disease and potential nano- or micro-metastases in the surrounding tissues and draining lymph nodes.

The release kinetics of nitric oxide from both the prodrug (NO 1) and the carrier-nitric oxide prodrug conjugate (acid-NO1) were determined in cell culture media. The half-life was determined by fitting the release data to a first order decay model using GraphPad 5 ($R^2$>0.97 for all fits, Table 2). The acid-NO1 exhibited a shorter release half-life compared to NO1, which is largely due to the initial burst release of NO. The poly(acrylic acid) star polymer backbone created a more acidic microenvironment surrounding the conjugates once they were solubilized in cell culture media, which triggered the liberation of NO immediately. Without the burst release, the acid-NO1 demonstrated a similar $t_{1/2}$ as NO1. Another NO-donating prodrug in preclinical studies, JS-K, has a NO release half-life of approximately 3.2 hours, which is shorter than the release $t_{1/2}$ of either the NO1 or the acid-NO1. All of the NO-prodrugs tested (JSK, NO1, NO2) exhibited significantly longer half-lives of NO release compared to the gaseous nitric oxide, which has a $t_{1/2}$ of 0.05 to 0.18 milliseconds in blood. According to Fetz et al, pretreatment of head and neck cancer cells using NO-donors, including S-nitroso-N-acetyl-penicillamine (SNAP), reverted the cells' cisplatin resistance via the modulation of survivin. Thus, a drug delivery platform that generates fast-releasing nitric oxide, along with slow-releasing platinum, may be a potential candidate for the delivery of synergistic cisplatin and nitric oxide combination chemotherapy.

TABLE 2

| Drugs/ conjugates | $IC_{50}$ in MCF-7 cells, μM | Release half-life, hours |
| --- | --- | --- |
| cisplatin | 20 ± 4 | — |
| Acid-Pt | >100 | 36.7‡ |
| NO1-prodrug | 48 ± 28 | 7.4* |
| Acid-NO1 | 64 ± 10 | 5.3* |

Table 2 shows the $IC_{50}$s and release half-lives of Acid-Pt, NO-prodrugs and Acid-NO.
‡Release half-life was determined in PBS with 10% serum at 37° C.
*Release half-lives were determined in cell culture media with MCF-7 cells.

Example 11

Cytotoxicity of Acid Star Polymers

Cell growth inhibition was determined in 96-well plates and reported in Table 2 above. Plates were seeded with 3,000 cells/well in 100 μL of media (12 replicates/sample). Drug or conjugate solutions were applied after 24 hours. Resazurin blue in 10 μL of PBS was applied to each well (final concentration 5 μM) after another 72 hours. After 4 hours, the well fluorescence was measured (ex/em 560/590) (SpectraMax Gemini, Molecular Devices), and the $IC_{50}$ concentration was determined as the midpoint between drug-free medium (positive) and cell-free (negative) controls.

The in vitro anti-proliferative activities of cisplatin, NO-donating prodrug, and their star polymer-based conjugates, including acid-Pt, acid-NO, and combinational acid-Pt/acid-NO were evaluated in cell culture using a human breast cancer cell line, MCF-7. Acid-NO conjugates demonstrated a similar $IC_{50}$ to the free NO-prodrug. Release of nitric oxide from the polymeric matrix inhibited the growth of cancer cells. The acid-Pt appeared to be less cytotoxic than cisplatin in the cells. This is likely due to the slow release of the active drug, which was not unexpected for a sustained-delivery platform. One of the obstacles that has not yet been overcome in infusion chemotherapy is the poor tumor penetration and accumulation of small-molecule anti-cancer agents. Usually the majority of the chemotherapeutics have been cleared from systemic circulation, via the kidneys, before a significant concentration of the anti-cancer agent is achieved in the tumorigenic tissues. However, the acid-Pt and acid-NO nanoconjugates may greatly enhance the intratumoral drug concentration compared to the normal tissues due to the Enhanced Permeability and Retention effect (EPR), in which nanoformulations tend to penetrate tumors more effectively via leaky, fenestrated tumor blood vessels. In addition, the acid-Pt and acid-NO formulations could be given subcutaneously as a local injection adjacent to the tumor to eradicate potential metastasis in the tumor-draining lymph nodes; whereas, it is clinically infeasible to inject free cisplatin or nitric oxide subcutaneously due to the severe tissue damage that the anticancer agents would create. After local injection of the acid-Pt, or the acid-NO, the multi-arm nanocarriers diffuse into the surrounding cutaneous tissues and enter the lymphatic vessels filled with lymph fluid; subsequently, they follow the lymph and reach the sentinel lymph node, the first tumor draining lymph node, and deliver the chemotherapeutics to the metastases. Furthermore, both of the star polymer-based conjugates could be given simultaneously as a localized combination therapy. Combination of NO and cisplatin has been shown to overcome drug resistance, sensitize cancer to radiation, and increase the anti-tumor activity of other chemotherapeutics, e.g., doxorubicin.

Example 12

Synthesis of 1,2;3,4-di-O-isopropylidene-6-O-acryloyl-α-D-galactopyranose (AIpGP)

In this example, 1,2;3,4-di-O-isopropylidene-6-O-acryloyl-α-D-galactopyranose (AIpGP) was synthesized. For example, to a 100-mL round bottom flask were added 1,2;3, 4-di-O-isopropylidene-α-D-galactopyranose (1.39 g, 5.20 mmol), basic alumina (2.44 g, 23.92 mmol), 20 mL of dry acetonitrile, and acryloyl chloride (2.26 mL, 27.04 mmol), dropwise. After stirring under argon for 3 days at ambient temperature, the mixture was filtered through a thin layer of celite, and the solids were washed with 50 mL of acetonitrile. The combined organic layers were concentrated under reduced pressure. The resulting pale yellow residue was purified through a flash column using 1:2 ethyl acetate:hexanes as eluents, and its molecular structure was verified by $^1$H-NMR and compared with the reported data.

Example 13

Synthesis of multi-arm poly-(6-O-methacryloyl-D-galactose) star polymer

Figure 14:
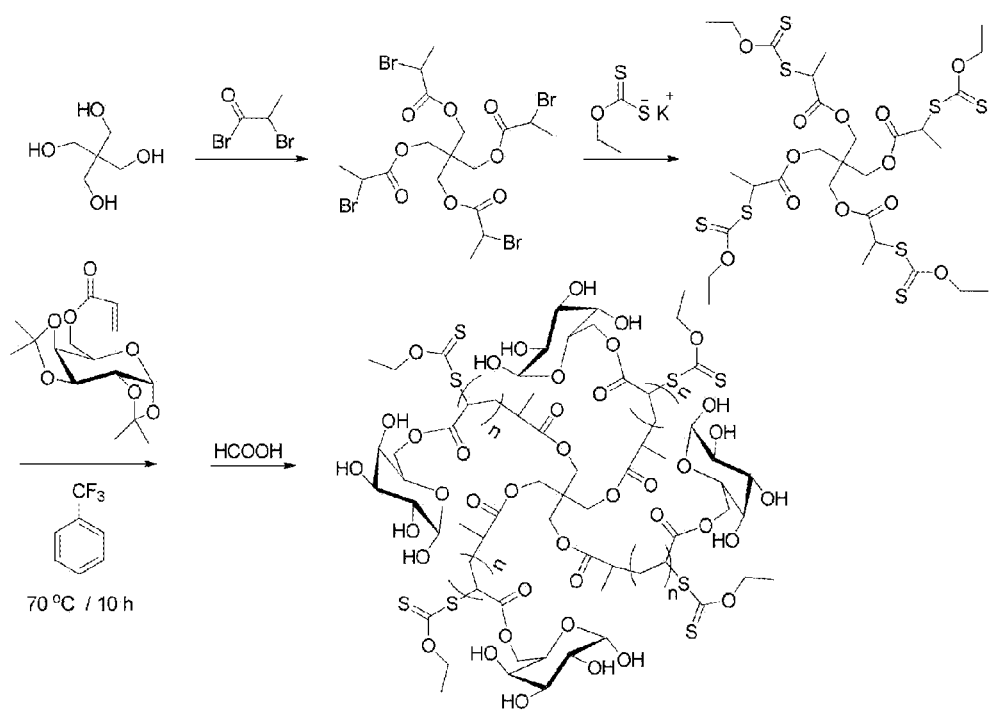
FIG. 14 includes a scheme of the synthesis of a multi-arm poly-(6-O-methacryloyl-D-galactose).

The multi-arm poly-(6-O-methacryloyl-D-galactose) star polymers were synthesized and reported in FIG. 14. In this example, the 1,2,3,4-di-O-isopropylidene-6-O-acryloyl-α-D-galactopyranose (3.11 g, 9.9 mmol) from Example 12 was treated with basic alumina and 10 mL of dry α,α,α-trifluorotoluene in a 50-mL round bottle flask. The RAFT agent (0.054 g, 0.0622 mmol) was added to the solution, followed by the addition of AIBN (1.36 mg, 0.00827 mmol), and the reaction flask was placed on ice and purged with argon for 30 min. The flask was then transferred to a thermostatic oil bath at 70° C. for ca. 10 hours. The mixture was cooled in an ice bath and poured into cold diethyl ether to obtain the precipitate followed by concentration under reduced pressure. The molecular structure and molecular weight of the resulting polymer were determined by $^1$H-NMR and size exclusion chromatography (SEC), respectively.

The poly-(1,2:3,4-di-O-isopropylidene-6-O-methacryloyl-α-D-galactopyranose) (500 mg) from Example 12 was dissolved in 100 mL of 90% formic acid. The solution was stirred at 60° C. for 24 hours. The solution then was dialyzed (10 kDa tubing) against distilled water for 2 days with water changes every 6 hours to remove the acid. After dialysis, the resulting polymer was lyophilized to obtain the desired multi-arm poly-(6-O-methacryloyl-D-galactose).

Example 14

Figure 15:
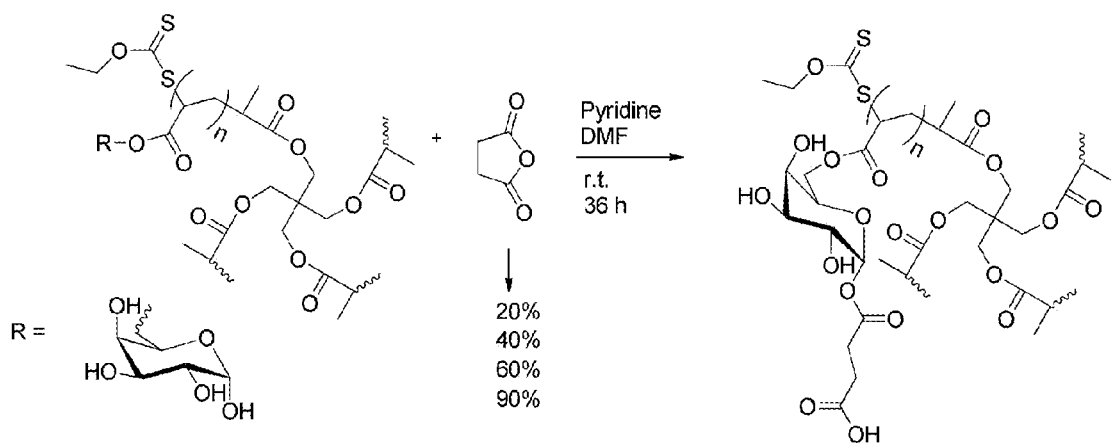
FIG. 15 includes a scheme of the synthetic modification of multi-arm poly-(6-O-methacryloyl-D-galactose) with succinic anhydride resulted in polymers with increasing degree of acid substitution. The degrees of acid substitution are 20, 40, 60, and 90% wt/wt.

Modification of Multi-Arm poly-(6-O-methacryloyl-D-galactose) with Succinic Anhydride The multi-arm poly-(6-O-methacryloyl-D-galactose) star polymers were modified using succinic anhydride and reported in FIG. 15. For example, polymers with increasing degrees of succination (20%, 40%, 60% and 90%) were generated by reacting the star poly-(6-O-methacryloyl-D-galactose) (100 mg) with succinic anhydride (20, 40, 60 and 90 mg, respectively) in 20 mL of dry dimethyl formaldehyde (FIG. 3). The mixtures were stirred at ambient temperature to form a homogeneous solution, followed by dropwise addition of 5 mL of dry pyridine. After 2 days, the solutions were dialyzed (10 kDa tubing) against 50% ethanoic water for 1 day followed by absolute ethanol for 1 day, with solvent changes every 6 hrs to remove the dimethyl formaldehyde, pyridine, and other small molecule impurities. Lyophilization of the resulting solution led to the desired sugar multi-arm polymers with increasing substitution degrees of carboxylic acids (20%, 40%, 60%, 90%).

Example 15

Figure 16:
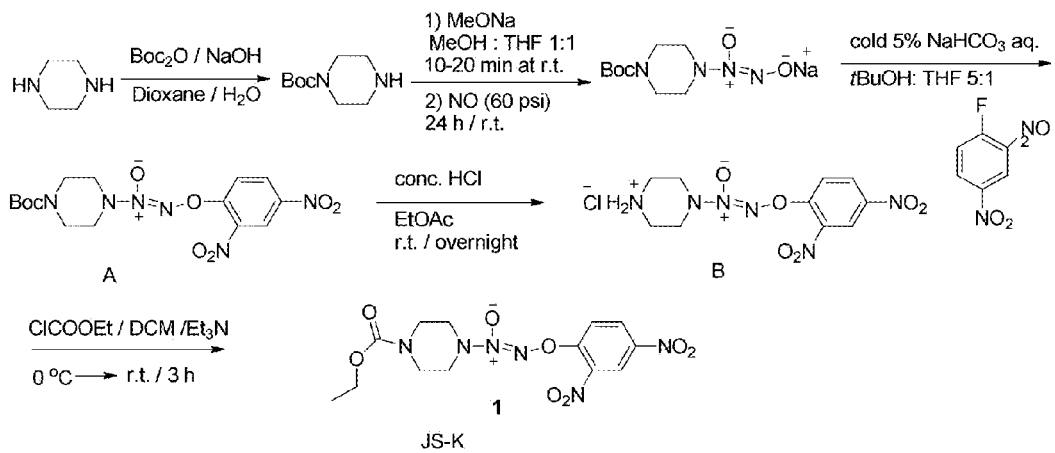
FIG. 16 includes a scheme of the synthesis of JS-K (compound 1). The nitric oxide donating prodrug JS-K, $O^2$-(2,4-Dinitrophenyl) 1-[(4-ethoxycarbonyl) piperazin-1-yl]diazen-1ium-1,2-diolate was synthesized.

Synthesis of Nitric Oxide Donating Prodrug JS-K, O$^2$-(2,4-Dinitrophenyl)1-[(4-ethoxycarbonyl)piperazin-1-yl]diazen-1ium-1,2-diolate The nitric oxide donating prodrug JS-K, O$^2$-(2,4-Dinitrophenyl) 1-[(4-ethoxycarbonyl)piperazin-1-yl]diazen-1ium-1,2-diolate was synthesized. The synthetic route is depicted in FIG. 16. For example, to a 250 mL round bottom flask were added 2.10 g of compound A (5.09 mmol) and 130 mL of ethyl acetate. After the mixture was cooled to 0° C., 11.5 mL of concentrated HCl was added dropwise. The reaction was allowed to warm to ambient temperature and stirred overnight. The resulting suspension was filtered and the yellow solid was washed with 100 mL of ethyl acetate and then dried under reduced pressure. The desired compound B was obtained without further purification, and the molecular structure was verified by $^1$H-NMR, $^{13}$C-NMR and high resolution mass spectrometry (HRMS).

Subsequently, compound B (0.132 g, 0.38 mmol) and ethyl chloroformate (56 μL, 0.57 mmol) were combined in 4 mL of dry THF. After cooling to 0° C., triethylamine (1.14 mmol) was added. The reaction was kept at 0° C. for 10 minutes and then stirred at ambient temperature for 3 hours or until TLC indicated complete consumption of starting material 2. The mixture was diluted with 10 mL of THF, and the organic phase was washed with water, saturated sodium bicarbonate solution and brine, and dried over sodium sulfate. Evaporation of the solvent under reduced pressure followed by purification of the residue using silica gel flash chromatography with 1:1 ethyl acetate:hexanes as eluents led to the desired compound JS-K (compound 1), and the molecular structure was verified by $^1$H-NMR, $^{13}$C-NMR and HRMS.

Example 16

Figure 17:
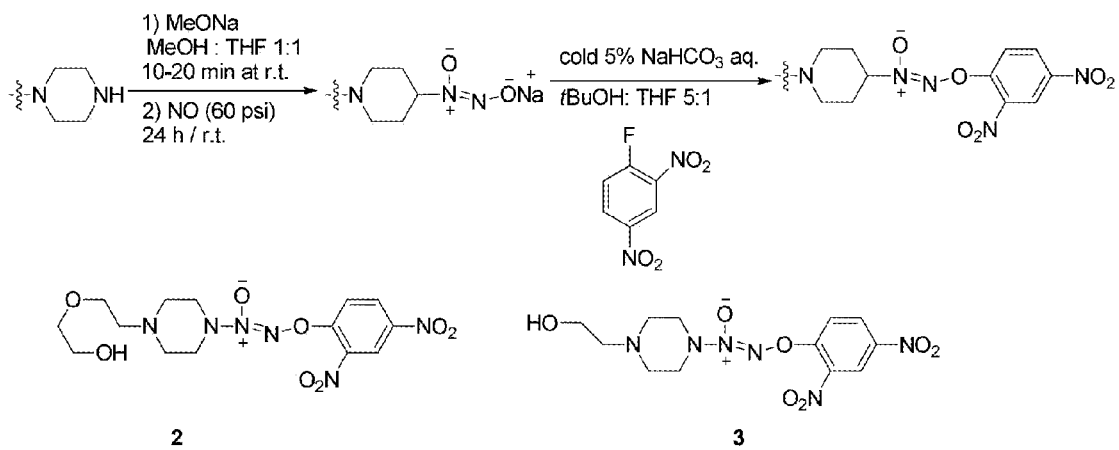
FIG. 17 includes a scheme of the synthesis of JS-K analogues (NO1: compound 2 and NO2: compound 3). The JS-K analogue 1 (NO1: compound 2), $O^2$-(2,4-Dinitrophenyl) 1-[{4-(2-(2-hydroxyethoxy))ethyl]piperazin-1-yl}diazen-1-ium-1,2-diolate, was synthesized. The JS-K analogue 2 (NO2: compound 3), $O^2$-(2,4-Dinitrophenyl) 1-[[4-(2-hydroxy)ethyl]-3-methylpiperazin-1-yl]diazen-1-ium-1,2-diolate, was synthesized.

Synthesis of JS-K analogue 2 (NO2), O$^2$-(2,4-Dinitrophenyl) 1-[[4-(2-hydroxy)ethyl]-3-methylpiperazin-1-yl]diazen-1-ium-1,2-diolate The JS-K analogue NO2 was synthesized and reported in FIG. 17 (Compound 3). For comparison, NO1 (from Example 5) is shown. For example, a solution of 1-(butyloxycarbonyl) homopiperazine (10 g, 50 mmol) in methanol (2 mL) was treated with 25% w/v methanolic sodium methoxide (9.3 mL) and ether (10 mL). The resulting solution was charged with 60 psi NO and stirred at ambient temperature for 24 hours. A white precipitate was filtered, washed with ether, and dried under reduced pressure to afford sodium 1-[(4-tert-butoxycarbonyl) homopiperazin-1-yl]diazen-1-ium-1,2-diolate, and the molecular structure was verified by $^1$H-NMR, $^{13}$C-NMR and HRMS.

It will be appreciated to those skilled in the art that other piperizine derivatives, such as hydroxylalkyl or hydroxyalkoxyalkyl (e.g., hydroxyethoxyethyl and hydroxyethyl) compounds illustrated, may be prepared in accordance with the present invention.

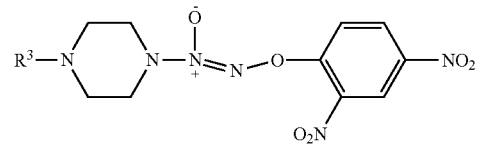

wherein R$^3$ is as hydroxylalkyl or hydroxyalkoxyalkyl.

Example 17

Synthesis of multi-arm poly-(6-O-methacryloyl-D-galactose)-acid-NO1 conjugate (multi-arm polymer-JS-K analogue NO1 conjugate)

Figure 18:
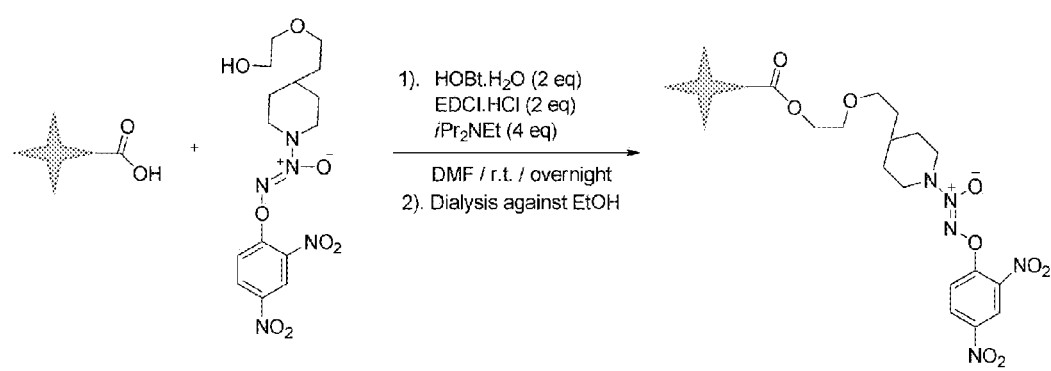
FIG. 18 includes a scheme of the synthesis of multi-arm sugar acid star polymer-JS-K analogue NO1 conjugate (sugar-NO1).

The multi-arm poly-(6-O-methacryloyl-D-galactose)-acid-NO1 conjugate was synthesized and reported in FIG. 18. For example, multi-arm poly-(6-O-methacryloyl-D-galactose) with 60% succination from Example 14 (50 mg) was dissolved in 25 mL of DMF: dd H$_2$O (25:1 v/v). After a homogeneous solution formed, EDCI.HCl (1.5 eq) and HOBt.H$_2$O (1.5 eq) were added and the temperature was kept at 0° C. After 5 minutes, JS-K analogue NO1 (1.0 eq) was added. The reaction proceeded at 0° C. for 30 minutes and then at ambient temperature overnight under argon. The resulting solution was dialyzed against 50% v/v ethanol in water for 12 hours and then absolute ethanol for 12 hours using 10 kDa dialysis tubing. Removal of the solvent under reduced pressure led to the desired conjugate, and the molecular structure and drug loading degree were determined by $^1$H-NMR.

The yield of the MADIX/RAFT polymerization reaction mediated by xanthates was ca. 90%. The NMR results demonstrated that the satisfactory conversion and polymerization were obtained when the reaction was allowed to proceed for 8 to 12 hours. After deprotection, the resulting sugar multi-arm polymer is highly soluble in water and organic solvents, including $CH_2Cl_2$, $CHCl_3$, DMF and THF. The sugar multi-arm polymers were further modified using succinic anhydride to yield multi-arm polymers with increasing degrees (20, 40, 60, and 90%) of terminal carboxylic acid groups on the polymer arms.

As discussed above, the nitric oxide prodrug JS-K (Example 15) and its two analogues (Example 5 for NO1 and Example 16 for NO2) were successfully synthesized; the yields of the reactions are. The NO1, $O^2$-(2,4-dinitrophenyl) 1-{[4-(2-(2-hydroxyethoxy))ethyl]piperazin-1-yl}diazen-1-ium-1,2-diolate, was selected to be further conjugated onto the sugar multi-arm polymer with 60% acid substitution, resulting in the formation of a multi-arm polymer-NO1 conjugate. The substitution degree of NO1 prodrug on the conjugate was determined to be approximately 12% (wt/wt) based on the ratio of the aromatic protons of the NO1 prodrug to the protons of the repeating units of the multi-arm polymer backbone.

Example 18

Characterization of Multi-Arm Sugar Star Polymers by Size Exclusion Chromatography The molecular weights and PDI of the multi-arm polymers and poly-(6-O-methacryloyl-R-D-galactpyranose) were determined using an EZStart 7.4 software and a Shimadzu 2010CHT system equipped with an RID-10A refractive index detector and a TSK gel multipore Hx-M 7.8×30 cm column. The mobile phase contained 10-mM LiCl in DMF (0.8 mL/min). The calibration curve was generated using polystyrene standards ranging from 1,180 to 339,500 g/mol. After deprotection, the resulting multi-arm poly-(6-O-methacryloyl-D-galactose) was highly soluble in methanol, water, DMF and DMSO. The molecular weights of the acid multi-arm polymers were determined by SEC using the same condition except that the system was calibrated using polyethylene glycol (PEG) standards ranging from 3,070 to 66,100 g/mol (Scientific Polymer Products, Inc). The degree of substitution was determined by $^1$H-NMR in MeOD, based on the ratio of the methylene protons of the acid groups to the protons of the sugar groups.

The molecular weight of the multi-arm poly-(1,2:3,4-di-O-isopropylidene-6-O-methacryloyl-α-D-galactopyranose) synthesized in Example 13 was determined by SEC using polystyrene polymers as standards. The number average molecular weight, $M_n$, and the PDI were determined to be 73,292 g/mol and 1.13, respectively (FIG. 19A). After the removal of the isopropylidene protecting groups within the multi-arm polymer, the molecular weight of the resulting multi-arm poly-(6-O-methacryloyl-D-galactose) (see Example 13) was determined by SEC under the same condition except that PEG polymers were used as standards. The $M_n$ and PDI were determined to be 45,460 g/mol and 1.20, respectively (FIG. 19B). After the modification of the multi-arm poly-(6-O-methacryloyl-D-galactose) with succinic anhydride (see Example 14), the resulting acid derivatives of the polymer were analyzed by SEC and their molecular weights and PDIs were reported in Table 3.

Example 19

Characterization of Multi-Arm Sugar Star Polymers by NMR

Figure 19:
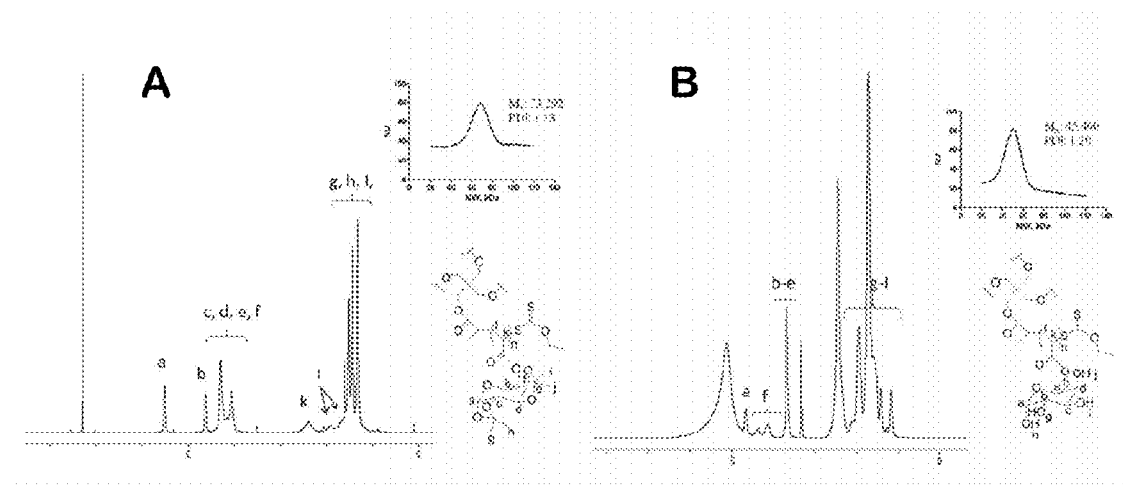
FIGS. 19A-19B include $^1$H-NMR spectra SEC traces of multi-arm poly-(1,2:3,4-di-O-isopropylidene-6-O-methacryloyl-α-D-galactopyranose) and multi-arm poly-(6-O-methacryloyl-D-galactose).

The molecular structures of the MADIX/RAFT agent (Example 1), 4-arm polymer (Example 13), acid derivatives of the 4-arm polymer (Example 14), JS-K and its analogues NO1 and NO2 (Examples 5, 15, 16), and the 4-arm polymer-NO conjugate (Example 17; sugar-NO1) were determined by $^1$H-NMR, $^{13}$C-NMR and HRMS and reported in FIG. 19 and Table 3. The substitution degrees of the acid on the sugar multi-arm polymer were determined by $^1$H-NMR based on the ratio of the methylene protons of the acid groups to the protons of the sugar groups. The following sugar acid polymers have been made successfully: sugar-20% acid, sugar-40% acid, sugar-60% acid, sugar-90% acid. In addition, the substitution degree of NO1 prodrug on the sugar-NO1 conjugate was also determined by $^1$H-NMR.

TABLE 3

| Acid % | $M_{theo}$, g/mol | $M_{n,\,GPC}$*, g/mol | PDI | Viscosity$_{1\,mg/mL}$, $mm^2 \cdot S^{-1}$ | Viscosity$_{10\,mg/mL}$, $mm^2 \cdot S^{-1}$ |
|---|---|---|---|---|---|
| 0 | 54,610 | 45,460 | 1.20 | 1.0557 | 1.0808 |
| 20 | 54,610 | 45,890 | 1.19 | 1.0473 | 1.1131 |
| 40 | 63,640 | 54,390 | 1.17 | 1.0488 | 1.1017 |
| 60 | 72,730 | 60,110 | 1.21 | 1.0451 | 1.0952 |
| 90 | 86,370 | 75,100 | 1.15 | 1.0536 | 1.1033 |

Table 3 shows the molecular weights, PDIs and viscosity of acid derivatives of sugar multi-arm polymer of Example 17.
*Standard: PEG; mobile phase: DMF (10 mM LiCl); flow rate: 0.8 mL/min.

Example 20

Solubility of Multi-Arm Sugar Star Polymer and Acid Derivatives

The water solubilities of multi-arm poly-(6-O-methacryloyl-D-galactose) and its acid-modified derivatives of Example 14 were measured in 1×PBS (pH 7.4) at 37° C. The solutions were kept under this condition and monitored for precipitation for 24 hours. The solubility of multi-arm sugar star polymers with different degrees of acid substitution is in a range from 250 to 320 mg/mL (i.e., 250, 260, 270, 280, 290, 300, 310, and 320 mg/mL).

The solubilities of sugar polymer poly-(6-O-methacryloyl-D-galactose) and its acid-modified derivatives were determined in pH 7.4 PBS at 37° C. The solubilities of multi-arm sugar star polymer with 0, 20, 40, 60, and 90% acid substitution were determined to be 250, 273, 295, 314, and 309 mg/mL, respectively. The result suggested a linear increase in the solubility with increasing degrees of acid substitution from 0-60% wt ($R^2$=0.998). In addition, the intrinsic solubility of the polymer with 90% acid substitution did not further increase and it appeared to exhibit a similar solubility as the polymer with 60% acid substitution.

Example 21

Viscosity of Multi-Arm Sugar Star Polymers

The viscosity parameters were measured using a Stabinger viscometer (SVM 3000, Anton Paar, USA). A series of sugar multi-arm polymer samples with or without acid modification (20%, 40%, 60%, and 90% wt/wt) were prepared by dissolving the polymers in dd $H_2O$ at three concentrations including:

1.0 mg/mL, 3.0 mg/mL and 10.0 mg/mL. The viscosity measurements are reported in Table 3 above.

The viscosities of sugar multi-arm polymer, poly-(6-O-methacryloyl-D-galactose), and its acid-modified derivatives (sugar polymers with 20%, 40%, 60%, and 90% acid substitution) were determined in ddH$_2$O at three increasing concentrations (1.0, 3.0, and 10.0 mg/mL). The polymers demonstrated low viscosities, merely 5-10% higher than pure H$_2$O, regardless of the percent of the acid substitution. Furthermore, the viscosities of various polymers with different degrees of acid substitution appeared to increase with increasing polymer concentrations from 1.0 to 10.0 mg/mL.

Example 22

Cytotoxicity of Multi-Arm Sugar Star Polymer Conjugates

Cell growth inhibition was determined in 96-well plates (3,000 cells/well in 100 µL, 12 replicates/sample) using highly invasive human breast cancer cells, MDA-MB-231, non-metastatic human breast cancer cells, MDA-MB-468, and highly invasive human head and neck squamous cell cancer cells positive for epithelia growth factor receptor, MDA-1986. Drug or conjugate solutions were applied after 24 hours, and 72 hours post-addition, resazurin blue in 10 µL of PBS was applied to each well (final concentration 5 µM). After 4 hours, well fluorescence was measured (ex/em 560/590) (SpectraMax Gemini, Molecular Devices), and the IC$_{50}$ concentration determined as the midpoint between drug-free medium (positive) and cell-free (negative) controls, and reported in Table 4.

TABLE 4

| Prodrugs/ conjugates | IC$_{50}$: MDA-1986 | IC$_{50}$: MDA-MB-468 | IC$_{50}$: MDA-MB-231 | Release half-life, h |
| --- | --- | --- | --- | --- |
| NO1 | 33 ± 1 µM | 26 ± 4 µM | 32 ± 3 µM | 7.1 |
| NO2 | 57 ± 6 µM | 27 ± 3 µM | — | 9.0 |
| JS-K | 16 ± 2 µM | 42 ± 4 µM | — | 3.2 |
| Sugar-NO1 | 86 ± 9 µM | 67 ± 6 µM | 120 ± 14 µM | 9.2 |

Table 4 shows the IC$_{50}$ values and release halflife of NO prodrugs (NO1, NO2 and JS-K) and multi-arm polymer-NO1 conjugates.

Example 23

Nitric Oxide Release from Multi-Arm Sugar Star Polymer Conjugates

Figure 20:
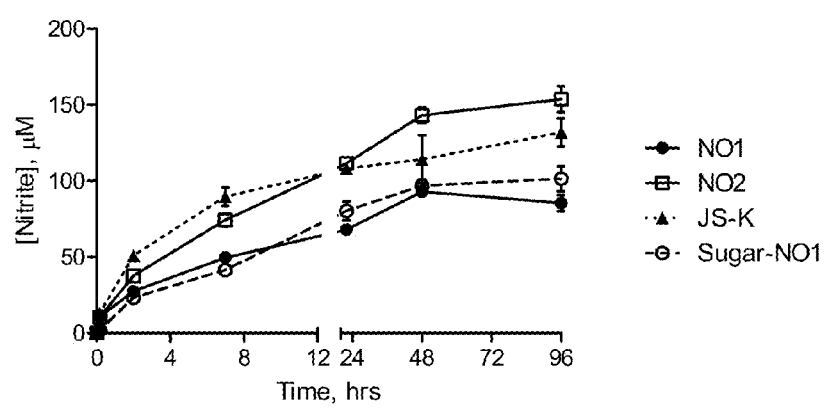
FIG. 20 includes a graph of the in vitro production of nitric oxide by NO1, NO2, JS-K, and sugar-NO1. The amount of NO released was determined by measuring the concentration of a stable NO breakdown product, nitrite. The starting concentration of all experiments is 20 μM on NO basis. The release studies were conducted in DMEM in the presence of MDA-1986 cells using a Griess assay. The release half-lives were determined to be 6, 7, 3, and 10 hours, for NO1, NO2, JS-K and sugar-NO1, respectively.

To determine the release half-life of nitric oxide from JS-K, NO1, NO2 and sugar-NO1, MDA-1986 cells were seeded in 96-well plates 24 hours prior to drug treatment (100 µL/well). On the following day, cells were treated with 20 µM of either one of the nitric oxide prodrugs (NO1, NO2 or JS-K) or the multi-arm polymer based nitric oxide prodrug conjugate number 1 (sugar-NO1). Fifty microliters of cell culture media were collected from each plate at 10 minutes, 2, 7, 22, 48, and 96 hours, post treatment to determine the nitrite content (N=5). The Griess reaction was performed according to the manufacturer's suggestions. The fluorescence intensity was measured between 520 and 550 nm using a fluorescence microplate reader. The nitrite concentration and the corresponding nitrite oxide levels were determined using a nitrite standard curve. The release half-lives were determined and reported in Table 4 and FIG. 20.

The release kinetics of nitric oxide prodrugs were determined in cell culture (DMEM with 10% bovine serum albumin and 1% L-glutamine) using human HNSCC cell line, MDA-1986. The concentration of nitrite, the stable breakdown product of gaseous nitric oxide, was measured using Griess assay as an indirect measurement of nitric oxide concentration in cell culture media. The assay is based on the reaction between sulfanilamide, N-1-napthyethylenediamine dihydrochloride and nitrite, under acidic conditions to produce a fluorescent azo compound. The halflife was determined by fitting the release data to a first order decay model using GraphPad 5 ($R^2$>0.96 for all fits). A nitrite calibration curve ($R^2$=0.99) was generated under the same condition using a series of nitrite solutions (0, 1.56, 3.13, 6.25, 12.5, 25, 50, and 100 µM).

All three nitric oxide prodrugs, NO1, NO2 and JS-K, as well as the sugar-NO1 conjugate, produced nitric oxide in a sustained manner, with generation half-lives of 7.1, 9.0, 3.2, and 9.2 hours, respectively.

Example 24

Tumor Model and Efficacy of Multi-Arm Sugar Star Polymer-NO1 Conjugates

The MDA-1986 human head and neck squamous cell carcinoma cells were prepared in PBS at a concentration of 2×10$^7$ cells/mL. Female nude mice were anesthetized with 1.5% isoflurane in 50% O$_2$:air mixture, and 50 µL of cell solution was injected into the sub-mucosa of the mice using a 30-ga needle.

The tumor cells were implanted at the same time for all groups of animals. The treatments began once the primary tumors reached 50 to 100 mm$^3$, which typically occurred within 2 weeks of implantation. The tumor growth was monitored 2 to 3 times weekly by measurement with a digital caliper in two perpendicular dimensions, and the tumor volume was calculated using the equation: tumor volume=0.52× (width)$^2$×(length). Animals were euthanized when their tumor size reached 1000 mm$^3$ or the body score index dropped below 2.

Figure 21:
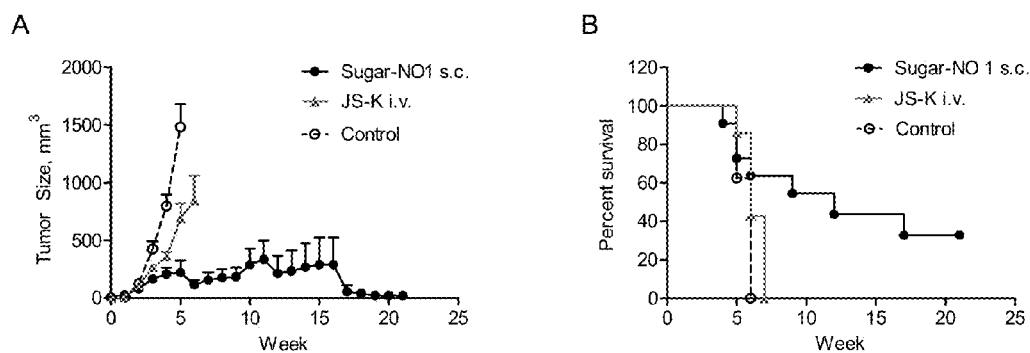
FIGS. 21A-21B include a graph of the size measurement of head and neck tumors and a graph of the survival rate of the animals.

Animals bearing head and neck tumors were randomly divided into 3 groups, including Sugar NO1 s.c. group (N=11), JS-K i.v. group (N=7) and untreated control group (N=8). The treatments were administered subcutaneously next to the tumor two week after tumor cell implantation, at a dose of 10 mg/kg on the basis of NO prodrugs. The results were reported in FIG. 21.

Animals in either the control group or the JS-K i.v. treatment group had tumors with a size of approximately 1000 mm$^3$, five or six weeks after tumor cell implantation, respectively. In comparison, the animals treated with sugar-NO1 developed a tumor of an average size of approximately 200 mm$^3$ within the same time frame, which is 5-fold smaller than the tumor sizes observed in the control and JS-K i.v. groups. Additionally, 32.7% of animals in the sugar-NO1 group survived the study (21 weeks post-tumor cell injection), and two mice had a complete response (defined as no evidence of residual disease) within 14 weeks. On the contrary, 100% of the control or JS-K treated animals were euthanized within 7 weeks either due to the tumor size exceeding 1000 mm$^3$ or necrosis of the injection site on the tail. Further, HNSCC tumor progression was delayed by nearly six weeks on average after s.c. sugar-NO1 therapy, and the survival rate was significantly extended relative to the control group (p<0.001). The disease condition of each individual animal in the control or treated groups is reported in Table 5.

TABLE 5

| Treatment Group | No. 1 | No. 2 | No. 3 | No. 4 | No. 5 | No. 6 | No. 7 | No. 8 |
|---|---|---|---|---|---|---|---|---|
| Sugar NO1 s.c. | PR | PD | CR | PD | PD | PR | CR | SD |
| JS-K i.v. | PD | Necrosis | PD | PD | Necrosis | PD | — | — |
| Control | PD | PD | PD | PD | PD | PD | PD | — |

Table 5 shows the disease condition of tumor bearing mice in control, i.v. JS-K and s.c. Sugar-NO1 treatment groups. Tumor response was reported based on modified RECIST criteria.
CR = Complete Response (no gross evidence of tumor);
PR = Partial Response (>30% reduction);
SD = Stable Disease (neither PR nor PD criteria met);
PD = Progressive Disease (>30% tumor growth).
Mice with an ulcerated tumor that were euthanized before the end of the study were excluded from this analysis.

Example 25

Synthesis of 17-((2-hydroxyethyl)amino)-17-demethoxygeldanamycin (17-HEAG)

Figure 27:
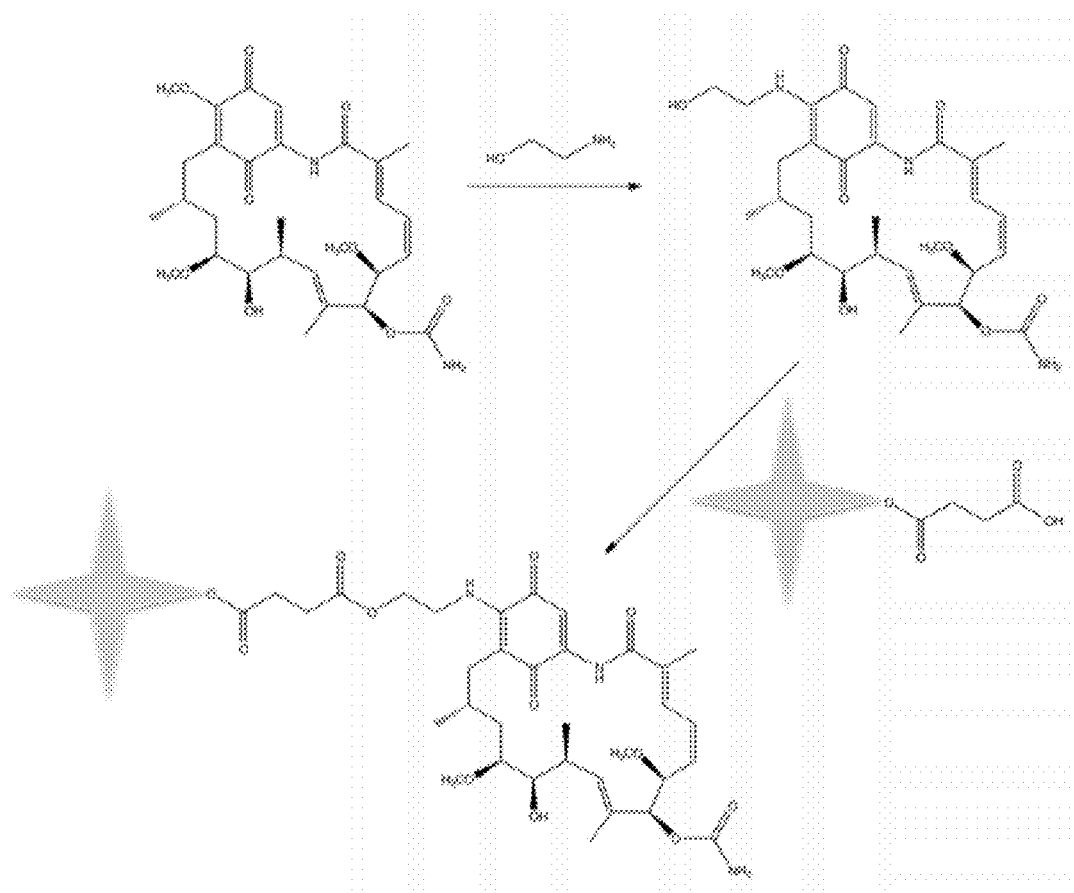
FIG. 27 includes a scheme of the geldanamycin reaction with ethanolamine to give the 17-HEAG analogue, followed by the reaction of 17-HEAG with the 60% acid-star polymer resulting in the Star-GA conjugate.

The 17-((2-hydroxyethyl)amino)-17-demethoxygeldanamycin (17-HEAG) was synthesized as shown in the first part of FIG. 27. For example, to a solution of geldanamycin (100 mg, 0.178 mmol) in dry chloroform (20 mL), ethanolamine (30 eq) was added dropwise. The reaction was protected from light and was allowed to proceed at ambient temperature (ca. 20° C.) under argon protection for 4 hours until the TLC showed complete consumption of the starting materials. The reaction mixture was then washed with 1-M HCl (100 mL) and dried over $Na_2SO_4$. The solvent was removed under reduced pressure, and the compound was used without further purification. $^1$H-NMR in $CDCl_3$ was used to confirm the structure, and the NMR spectrum was consistent with the reported data and showed the compound was determined to be pure. The desired 17-((2-hydroxyethyl)amino)-17-demethoxygeldanamycin analogue (17-HEAG) was obtained as a purple solid (101 mg, 96%).

Example 26

Synthesis of Star-GA

Sugar-acid-star polymer (60% acid) (72 mg) was dissolved in dry DMF (20 mL) and was cooled to 0° C. EDAC (65.2 mg, 0.34 mmol) and $HOBt.H_2O$ (52.3 mg, 0.34 mmol) were added to the polymer solution. After five minutes, the 17-HEAG analogue (100 mg, 0.17 mmol) was added in one portion. The reaction was protected from light and allowed to proceed at room temperature (ca. 20° C.) overnight. The resulting solution was dialyzed (MWCO 10 kD, SpecraPor 7, Spectrum Laboratories) against EtOH: $H_2O$ (1:1) for 12 hours with solvent exchanges every 3 hours followed by dialysis against 100% EtOH for 6 hours with solvent exchanges every 3 hours. The solvent was removed under reduced pressure yielding the pure star-GA conjugate (FIG. 27).

Figure 28:
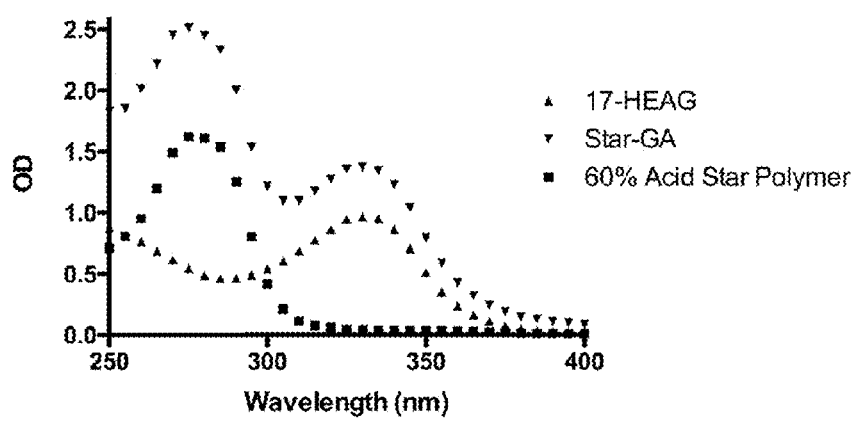
FIG. 28 includes the UV absorbance spectra of 17-HEAG, 60% acid-star-polymer, and star-GA conjugate in methanol. (Note: sample concentrations were not held constant, thus the relative intensities cannot be compared).

The conjugation degree of 17-HEAG to the star polymer was determined by $^1$H-NMR (Bruker, 400 MHz) in MeOD and UV spectroscopy (SPECTRA MAX PLUS, Molecular Devices) at 330 nm using a standard calibration curve (1-30 μg/mL) in MeOH (FIG. 28). The conjugation degree was determined by comparing the ratio of the proton on the C19 position on the benzoquinone ring with the proton of the repeating unit of the star polymer from the $^1$H-NMR spectra.

The degree of conjugation of 17-HEAG to the star polymer was determined to be 15 wt % by $^1$H-NMR in MeOD and 14.8 wt % by UV spectroscopy at 330 nm using a standard calibration curve (1-30 μg/mL). The conjugation degree was determined by comparing the ratio of the proton on the C19 position on the benzoquinone ring with the proton of the repeating unit of the star polymer from the $^1$H-NMR spectra. A series of 17-HEAG concentrations were prepared from a stock solution of 17-HEAG in MeOH. The concentrations used for the standard curve of 17-HEAG were 1, 2, 5, 8, 10, 20, and 30 μg/mL ($R^2$=0.997) in MeOH. The absorbance of the star-GA was measured at 330 nm, and the resulting optical density measurements were due to the absorbance of 17-HEAG and not the star polymer, as the star polymer does not exhibit UV absorbance at 330 nm. The loading degree of 17-HEAG was calculated to be 14.8% (wt/wt); and the same batch of the star-GA was used for all experiments unless otherwise noted.

The loading degree of 15% wt/wt of 17-HEAG on the star polymer limited the water solubility of the conjugate to a minimum requirement of 30% DMSO for solubilization at the concentrations needed for treatment. Higher loading degrees of 27 and 31% were also synthesized, however these conjugates were not continued with due to the lack of water solubility even in high DMSO concentrations. The maximal drug loading of 15% observed with 17-HEAG in order to maintain sufficient water solubility without solvent.

Example 27

In Vitro Release

Figure 29:
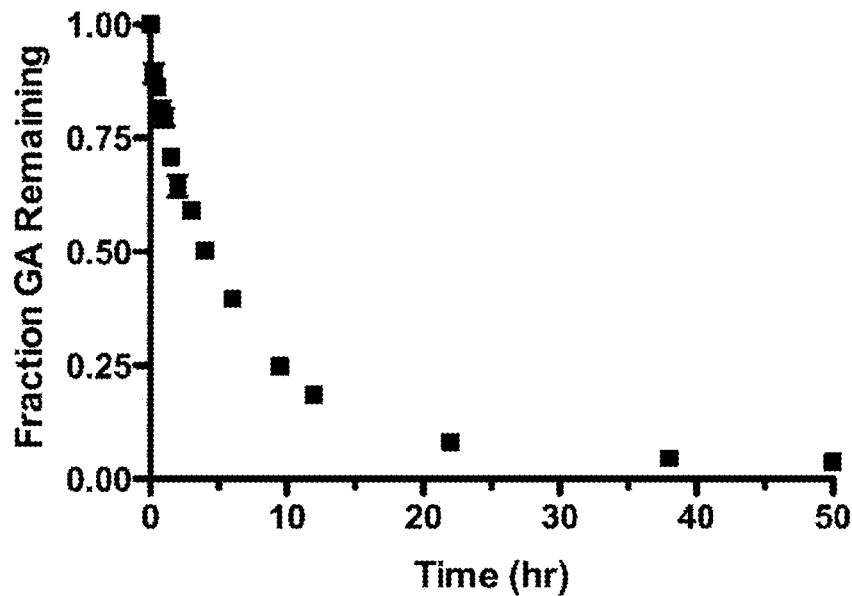
FIG. 29 includes a graph of the release kinetics of 17-HEAG from the star-GA conjugate in PBS at 37° C. (n=3).

Star-GA was dissolved in PBS at a GA concentration of 0.075 mg/mL (0.5 mg/mL total conc.) and was sealed in a dialysis bag (3500 MWCO, n=3, Pierce). The dialysis bags were placed in a temperature controlled bath set to 37° C. containing PBS under sink conditions; the bath was protected from light for the experiment duration. At predetermined time intervals, 150 μl, aliquots were taken from the bags for 50 hours and were placed at −20° C. until analysis. The release samples were analyzed using a UV absorbance detector with a 17-HEAG standard curve (0.8 to 80 μg/mL, 11 concentrations). The release samples were diluted to 200 μL with PBS (3:4 dilution), the 17-HEAG standard curve dilutions (n=2), PBS (n=2), and the release samples (n=3) were added to a 96-well plate, and the UV absorbance of the plate was measured at 330 nm on a UV plate reader (SPECTRA MAX PLUS, Molecular Devices) (FIG. 29).

The star-GA conjugate was synthesized using an ester linkage, and hydrolysis of the ester bond will lead to the release of 17-HEAG from the star polymer platform. The release samples were analyzed using a UV plate reader using a 17-HEAG standard curve. A series of 17-HEAG concentrations in PBS were prepared from a stock solution of 17-HEAG. The concentrations used for the standard curve of 17-HEAG were 0.8, 1, 2, 4, 6, 8, 10, 20, 40, 60, and 80 μg/mL ($R^2$=0.999). The 17-HEAG concentrations for each release sample were calculated and normalized to the change in concentration due to sampling and osmosis, followed by normalization to the fraction of bound GA remaining in the dialysis bag. The fraction of GA bound to the star polymer was graphed as a function of time; after fitting the data to a one-phase exponential decay function (GraphPad Prism 10), it was found that the release half-life was 4.12±0.35 hr ($R^2$=0.99).

Example 28

In Vitro Cytotoxicity

B16F10 (lymphatically metastatic murine melanoma), MDA-MB-231 (human breast cancer), and HUVEC (normal human endothelial) cell lines, were maintained in Dulbecco's modified Eagle's medium (DMEM) supplemented with 1% L-Glutamine and 10% bovine growth serum in 5% $CO_2$ atmosphere. The HER2-expressing murine breast cancer cell line, 4T1.2 Neu was maintained in DMEM supplemented with 1% L-Glutamine, 10% bovine growth serum, and 500 µg/mL of G418 (geneticin) in 5% $CO_2$ atmosphere. The lymphatically metastatic human melanoma cell line, A2058 was maintained in low sodium bicarbonate (1.5 g/L) containing DMEM supplemented with 1% L-Glutamine, 10% bovine growth serum in 5% $CO_2$ atmosphere.

Prior to cell growth inhibition studies, cells were trypsinized and seeded at 3000 cells/well into 96-well tissue culture plates. After 24 hours, geldanamycin, 17-DMAG, 17-AAG, 17-HEAG, Star-GA (GA basis), or melphalan hydrochloride dilutions in 1×PBS (Fisher BioReagents, pH 7.4) with up to 3% DMSO (final well concentration, for the highest drug concentration) were added to the B16F10, A2058, HUVEC, 4T1.2 Neu, or MDA-MB-231 cells (n=8 or 12, 10 µL/well, 8 or 6 concentrations $10^{-10}$ to $10^{-3}$ M, respectively). Solutions of 10% trichloracetic acid was used as a negative control, media was used as a positive control, and 3% DMSO was used as an additional control (n=8 or 12, 10 µL/well). At 72 h post addition, 10 µL of resazurin blue in PBS was added (5 µM final concentration) to each well. After 3 hours, well fluorescence was measured ($\lambda_{ex}/\lambda_{em}$=560/590 nm) (SpectraMax Gemini, Molecular Devices). $IC_{50}$s were determined using the nonlinear regression curve fit of a one-site competition (GraphPad Prism 10).

The calculated $IC_{50}$ values for geldanamycin, 17-DMAG, 17-AAG, 17-HEAG, star-GA, 60% acid-star polymer, and melphalan, in the B16F10, A2058, HUVEC, 4T1.2 Neu, and MDA-MB-231 cell lines are reported. Melphalan was compared to geldanamycin analogues in the melanoma cell lines, as it is used clinically in the ILP treatment of melanoma. Geldanamycin and its derivatives exhibited similar cytotoxicity in the B16F10 and 4T1.2 Neu murine cell lines. The HUVEC and MDA-MB-231 cell lines were investigated to compare the cytotoxicities observed in the B16F10, A2058, and 4T1.2 Neu cell lines to a normal and human breast cancer cell line, respectively. In the B16F10 cell line, the 17-HEAG analogue exhibited similar cytotoxic effects as the parent drug GA. Similarly, the star-GA conjugate exhibited less toxicity than GA, 17-DMAG, and 17-AAG in the A2058 human melanoma cell line, but exhibited two orders of magnitude more toxicity than melphalan. All of the GA analogues and the star-GA exhibited similar toxicities in the 4T1.2 Neu HER2 expressing murine breast cancer cell line.

TABLE 6

$IC_{50}$s

| Drug | Cell lines | | | | |
|---|---|---|---|---|---|
| | B16F10 | A2058 | HUVEC | 4T1.2 Neu | MDA-MB-231 |
| geldanamycin | 36 nM | 44 nM | 440 nM | 260 nM | 963 nM |
| 17-DMAG | 250 nM | 44 nM | 29 µM | 296 nM | 189 nM |
| 17-AAG | 825 nM | 53 nM | 64 µM | 315 nM | N/A |
| star-GA | 290 nM | 375 nM | 1.4 µM | 335 nM | 580 nM |
| 60% acid-star polymer | 15 µM | 19 µM | 18 µM | N/A | N/A |
| melphalan | 103 µM | 30 µM | 209 µM | N/A | N/A |

Example 29

Anticancer Efficacy in B16F10 Murine Melanoma Tumor Bearing Mice

Figure 30:
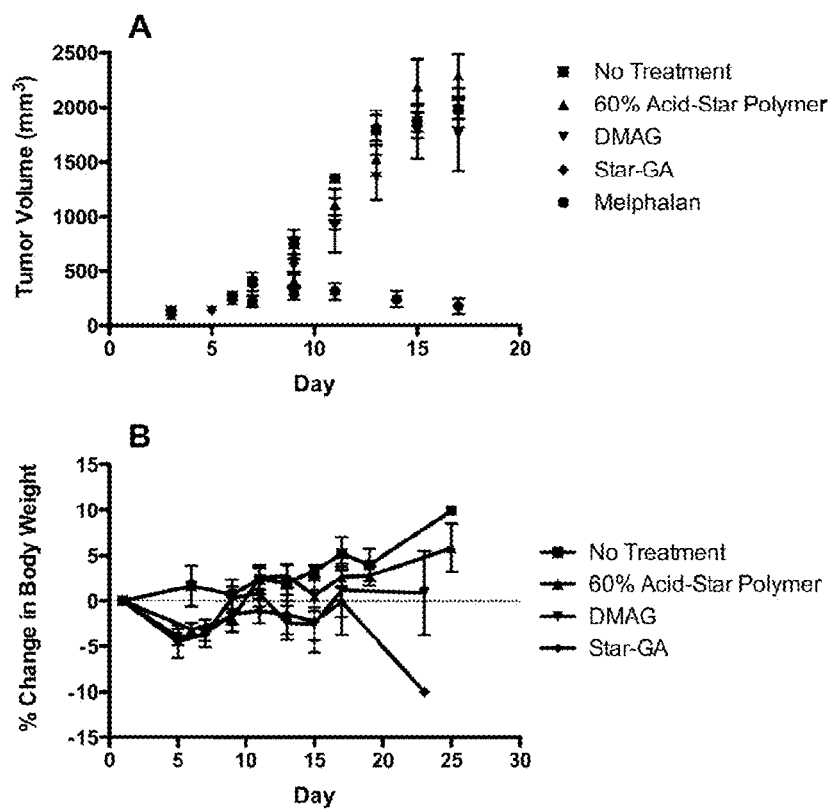
FIG. 30 includes the size measurements of tumors.

B16F10 cells were trypsinized (0.25% w/v trypsin), and diluted in sterile 1×PBS. Fifty microliters of a $1.1×10^8$ cells/mL suspension of B16F10 cells were injected ($5.5×10^6$ cells) s.c. into the right hind thigh of female Balb/c mice (20-25 g, Charles River, Wilmington, Mass.) under isoflurane anesthesia (Day 1). The tumors were measured and recorded, the volumes were calculated using the equation: Tumor Volume ($mm^3$)=0.52×(width)$^2$×length. When the B16F10 tumors reached 200-350 $mm^3$ (ca. Days 6-9), mice were randomly divided into five treatment groups: melphalan (i.v., n=5), 17-DMAG (i.v., n=4), star polymer (s.c., n=6), Star-GA (s.c., n=7), or no treatment (n=4) (FIG. 30).

Mice in the melphalan treatment group were injected once with melphalan (5 mg/kg) intravenously via the tail veil under isoflurane anesthesia. The formulation used to treat mice bearing B16F10 tumors was modified slightly from the product insert for ALKERAN (melphalan hydrochloride) for injections into humans. Melphalan was dissolved in concentrated hydrochloric acid (35-38%) to give a 15 mg/mL solution. The melphalan solution was then aliquoted into vials to give 0.75 mg melphalan/vial, and was dried using a speedvac concentrator (Labconoco) for 1.5 hours at 35° C. followed by 1 hour at ambient temperature. The vials containing dry melphalan hydrochloride were sealed and placed at −20° C. until further use. The reconstituted solution was prepared by first pre-sterilizing propylene glycol, 95% ethanol, and 0.02 g/mL sodium citrate solution, using a sterile syringe fitted with a 0.22 µm sterile filter (Millex GP PES membrane sterile filter, Millipore) into a sterile falcon tube. Then the reconstituted solution was prepared by combining 6 mL sterile propylene glycol, 0.52 mL sterile ethanol (95%), and 3.48 mL sodium citrate solution, and the solution was mixed well and filtered a second time with at 0.22 µm sterile filter. Immediately prior to injection, the 150 µL of the sterile reconstituted solution was rapidly added to the melphalan hydrochloride, the vial was immediately shaken vigorously until dissolved, followed by the rapid addition of 150 µL of sterile saline yielding a 2.5 mg/mL melphalan solution. The melphalan was dosed within 10 to 15 minutes after reconstitution to minimize degradation.

17-DMAG was dissolved in sterile DMSO and administered i.v. via the tail vein at a dose of 15 mg/kg (MTD). Star-GA was dissolved in a 1:1 mixture of DMSO:PBS, and the pH was adjusted to ca. 5.7 with NaOH, giving a Star-GA solution in 30% sterile DMSO and 70% sterile PBS, the Star-GA solution was administered at an equivalent dose to the 15 mg/kg 17-DMAG (13.64 mg/kg 17-HEAG, 15 wt % loading, i.e., 90.93 mg/kg total conjugate) with one peritumoral injection. Finally, the 60% acid-star polymer was dissolved in sterile PBS and the pH was adjusted to 5.4 with 2-M sterile NaOH, the 60% acid-star polymer was then administered at an equivalent polymer dose to the Star-GA (i.e., 77.29 mg/kg star polymer) with one peritumoral injection.

Figure 31:
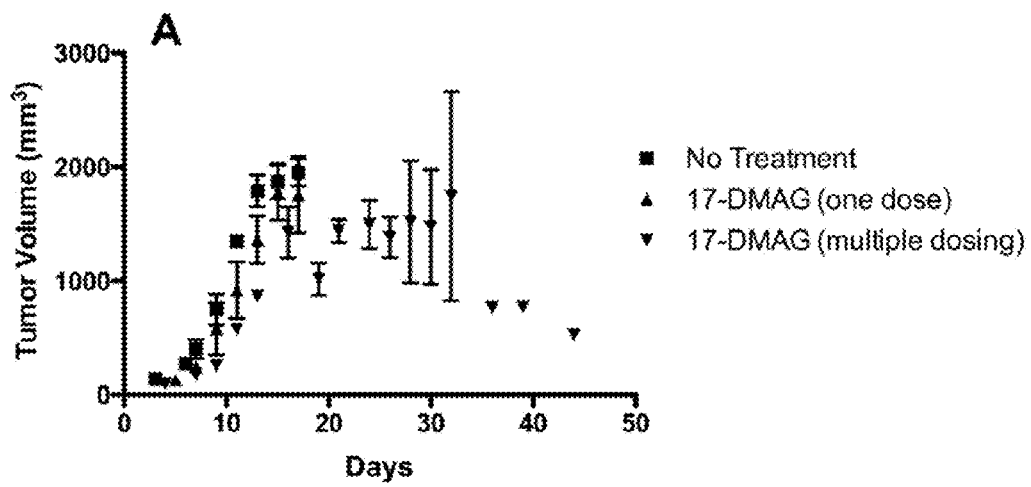
FIG. 31 includes the tumor growth curves of mice bearing B16F10 were treated with no treatment (red, n=4), one dose of 17-DMAG (i.v. 15 mg/kg, green, n=4), or three weekly doses of 17-DMAG (i.v. 3×5 mg/kg, blue, n=2).

In a preliminary multiple dosing study, mice bearing 100 mm³ B16F10 tumors (n=2) were treated with three weekly doses of 17-DMAG (i.v. in 1:1 DMSO:PBS) of 5 mg/kg each via the tail vein. The tumor growth was measured every two days and the tumor volumes were recorded (FIG. 31).

The hind flank as a primary tumor location is in contrast to most published reports of cell implantation into the hind footpad of mice to develop lymphatic metastases, where $2 \times 10^5$ cells are subcutaneously injected into the hind footpad and tumors develop to be 2 to 6 mm in diameter within three weeks. However, the hind thigh was chosen for both humane reasons and as a representative model for localized melanoma. Whereas, implantation into the hind footpad not only limits the mobility of the mouse but also is less likely to be a representative model of the natural progression of melanoma metastases. The footpad model would be representative of a locally advanced lymphatic metastatic model and was developed to intentionally form metastases within the lymph nodes by nature of the subcutaneous cell injection, which allows the B16F10 cells to directly drain into the rich lymphatic network in the mouse footpads leading to popliteal metastases.

Mice bearing B16F10 tumors with no treatment exhibited extremely rapid tumor growth, which reached 2000 mm³ by 19 days post implantation. On the contrary, mice treated with i.v. melphalan exhibited a complete response to treatment (p=0.0068, two-tailed unpaired t-test), which was statistically significant, with signs of tumor regression within two days post-treatment. Further, treatment with melphalan did not exhibit a relapse in tumor growth. In contrast, treatment with 17-DMAG, star-GA, or 60% acid-star polymer, did not exhibit statistically significant tumor growth inhibition in comparison to non-treated mice. Although both the 17-DMAG and Star-GA treatments demonstrated a 400-fold and 24-fold, respectively, increase in vitro toxicity in comparison to melphalan in the B16F10 cell line; the in vivo B16F10 tumors did not exhibit the same trends in tumor response.

Treatment with star-GA treatments led to a decrease in the mouse's body weight, compared to an increase in body weight observed for the mice treated with either 60% acid-star polymer or non-treated. However, the loss in body weight after treatment with star-GA was not observed until day 23, which corresponds to only one animal with a decrease in its body weight, and was not statistically significant. The remainder of the mice in the star-GA treatment group did not exhibit more than ±5% change in body weight, whereas the one mouse had a 14% decrease in body weight post-treatment. No physical signs of toxicities were seen with either the star-GA or 60% acid-star treatments; however, all mice treated with i.v. 17-DMAG displayed signs of tail necrosis, possibly due to extravasation of either the DMSO or 17-DMAG into the subcutaneous space of the tail. Although 17-DMAG has increased water solubility compared to the parent drug, GA, the concentrations needed for a 15 mg/kg dose with an injection volume of ca. 50 μL i.v. exceeded the water solubility of 17-DMAG, thus the need for DMSO in the injection of 17-DMAG.

Example 30

Anticancer Efficacy in 4T1.2 Neu Murine Breast Cancer Tumor Bearing Mice

Figure 32:
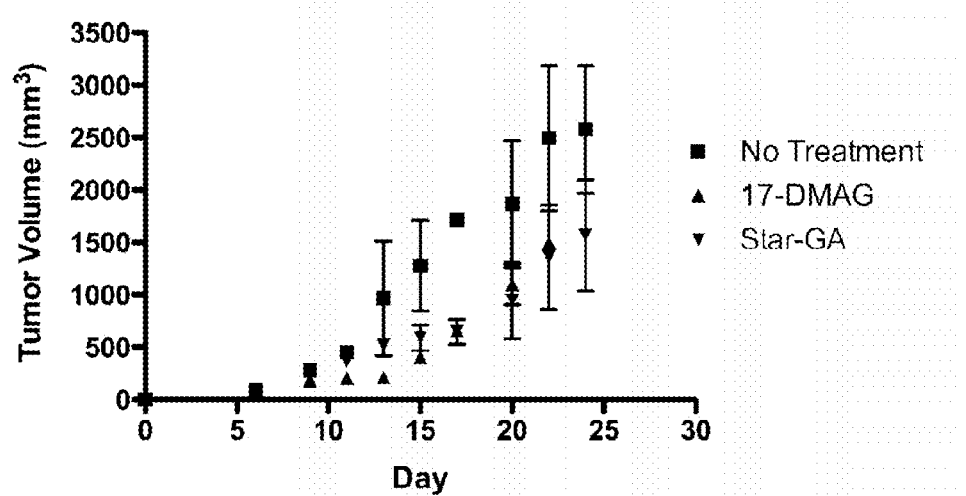
FIG. 32 includes a graph of the 4T1.2 Neu tumor growth in a pilot study after treatment with 17-DMAG (i.v. 10 mg/kg, n=2), Star-GA (s.c. 10 mg/kg 17-DMAG equivalent, n=3), and no treatment (n=2).

During cell preparation of the 4T1.2 Neu cells for implantation, G418 free media was used. Prior to tumor implantation, the hair surrounding the right upper portion of the mouse's chest was removed with depilatory cream. Female Balb/c mice (20-25 g, Charles River) were injected in the first mammary fat pad on the right side with 50 μL of a $2 \times 10^7$ cell/mL suspension in 1×PBS ($1 \times 10^6$ 4T1.2 Neu cells/animal) under isoflurane anesthesia (Day 1) (FIG. 32).

Example 31

Increased Maximum Tolerable Dose (MTD) of Star-GA

Four healthy female Balb/c mice (20-25 g, Charles River) were randomly divided into two groups and were dosed with two s.c. injections on either side of the first nipple on the right side with either 30 or 50 mg/kg Star-GA (17-HEAG basis, 31 wt % loading) in 30% DMSO and 70% PBS. Mice were monitored for at least one week for signs of toxicity, including losses in body weight, rough coat, fecal/urine soiling of the coat, diarrhea or dehydration, abnormal breathing patterns, or self-isolation.

Example 32

Anticancer Efficacy in 4T1.2 Neu Tumor Bearing Mice

Figure 33:
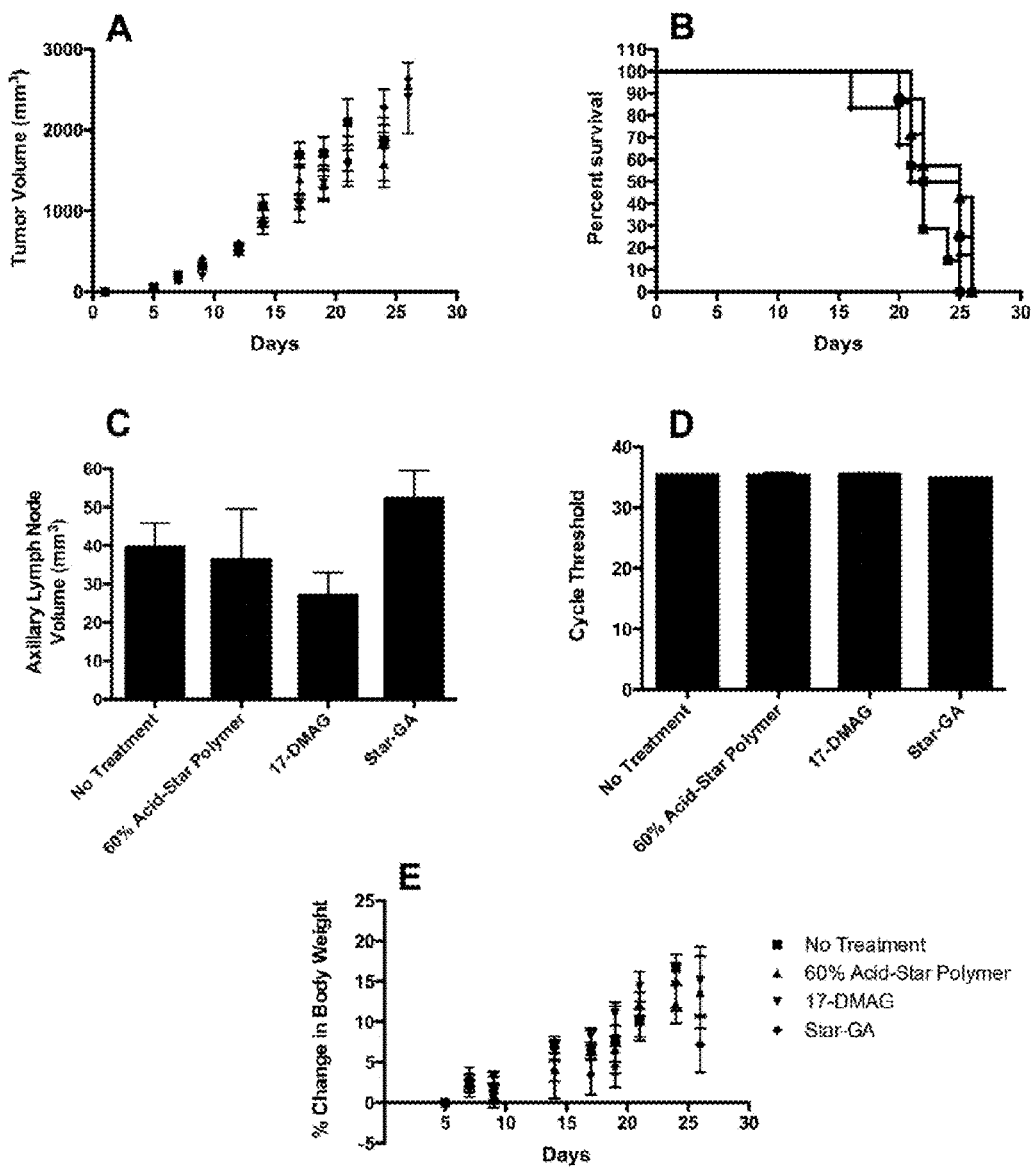
FIG. 33 include graphs of tumor measurement, survival rate, and rtPCR results. A) 4T1.2 Neu tumor growth in mice treated with 17-DMAG (i.v. 10 mg/kg, n=7) (green inverted triangles), Star-GA (s.c. 45 mg/kg 17-DMAG equivalent, n=8) (blue diamonds), 60% acid-star polymer (s.c. equivalent star polymer dose to 45 mg/kg Star-GA, n=7) (purple triangles), and no treatment (n=7) (red squares). B) 4T1.2 Neu survival curve after treatment with 17-DMAG (green inverted triangles), Star-GA (blue diamonds), 60% acid-star polymer (purple triangles), and no treatment (red squares). C) Right axillary lymph node volumes from mice treated with 17-DMAG (green), Star-GA (blue), 60% acid-star polymer (purple), and no treatment (red) after primary tumors reached 2000 mm$^3$. Axillary lymph node volume=0.52×(width)$^2$×(length). D) Metastatic assessment of HER2 expression in axillary lymph nodes from mice treated with 17-DMAG (green), Star-GA (blue), 60% acid-star polymer (purple), and no treatment (red) by rtPCR, representative cycle threshold values for HER2 expression in each treatment group. E) Percent change in body weight in mice bearing 4T1.2 Neu tumors after treatment with 17-DMAG (green inverted triangles), Star-GA (blue diamonds), 60% acid-star polymer (purple triangles), and no treatment (red squares).

Seven week old (18-22 g) female Balb/c mice purchased from Jackson Laboratory (Bar Harbor, Me.) were used in this study. On Day 7, when tumors reached 100-250 mm³, mice were randomly divided into four treatment groups, consisting of no treatment (n=7), 60% acid-star polymer (n=5), 17-DMAG (n=7), and Star-GA (n=8). The 17-DMAG was dosed at 10 mg/kg i.v. as a 1:1 sterile DMSO:PBS solution. Star-GA was dosed at 45 mg/kg (17-HEAG basis, 15% loading, 300 mg/kg Star-GA conjugate), in sterile 35% DMSO and 65% PBS, which was divided into two peritumoral injections on either side of the mammary tumor. Finally, the 60% acid-star polymer was dosed at an equivalent star polymer concentration used for the 45 mg/kg Star-GA (255 mg/kg 60% acid-star polymer), which was divided into two peritumoral injections onto either side of the mammary tumor. Tumor volumes were monitored and reported every two days (FIG. 33).

With doses of 30 and 50 mg/kg star-GA (17-HEAG basis), no visual signs of toxicity were observed with either treatment groups within one week post treatment. Further, after three weeks post dosing, no visual signs of toxicity were observed. Concentrations above 50 mg/kg were not investigated; however, it is possible that the MTD of the star-GA conjugate is higher than 50 mg/kg, on a 17-HEAG basis. Further studies with the use of 50 mg/kg Star-GA (17-HEAG basis) will be used for the treatment of 4T1.2 Tumors with an increase in the number animals per treatment group.

To minimize the occurrence of necrotic tails upon dosing 17-DMAG, as observed in the B16F10 in vivo study described in the previous section, 17-DMAG was dosed at 10 mg/kg i.v. in a 1:1 sterile DMSO:PBS solution rather than 15 mg/kg in 100% DMSO. A dose of 45 mg/kg was used as opposed to the 50 mg/kg in the MTD study due to solubility issues and limited quantities of the Star-GA conjugate.

Although the MTD of the star-GA conjugate was increased from 15 mg/kg 17-DMAG to at least 45 mg/kg 17-HEAG by utilizing the star-GA conjugate, no statistically significant increases in efficacy were depicted by a delay in tumor response or increased survival were observed with the star-GA conjugate compared to both non-treated and i.v.

17-DMAG treatment groups. In fact, no statistical significances were seen in regards to the tumor response with all three of the treatment (star polymer alone, 17-DMAG, or star-GA) compared to the non-treated mice. In addition, neither 17-DMAG nor star-GA treatments exhibited an increase in survival. Further, all but two mice, one treated with the 60% acid-star polymer and the other treated with the star-GA conjugate, exhibited an increase in body weight throughout the duration of the study. The two aforementioned mice exhibited a decrease in body weight coupled with a significant decrease in body score (body score of 1 or lower). A body score of 1 is representative of a mouse that appears to be emaciated, with a prominent skeletal structure with little flesh covering, and distinctly segmented vertebrae. The cause of the low body score in these two mice was not further investigated.

Example 33

Metastatic Analysis of Axillary Lymph Nodes by Nodal Volume and Real Time Polymerase Chain Reaction (rtPCR)

The metastatic state of the 4T1.2 Neu tumor model post treatment was assessed by axillary lymph node volume and the nodal HER 2 expression. The visible axillary lymph nodes on the right side were harvested from mice in each treatment group (17-DMAG, 60% acid-star polymer, Star-GA, and no treatment, dosing for each treatment group described in Example 32 once the mice reached a humane endpoint, i.e., tumor volume >2000 mm$^3$, body score index of 1, or signs of necrosis or toxicity. The mice were euthanized and the nodes were flash frozen and stored at −80° C. until real-time PCR (rtPCR) analysis. The lymph nodes were measured with digital calipers and the axillary lymph node volumes were calculated using the same equation used to calculate tumor volume, i.e., volume=$0.52\times(\text{width})^2\times(\text{length})$.

The total RNAs from the frozen lymph node samples were extracted using TriZol reagent (Invitrogen). The first-strand cDNA was synthesized using the Omniscript-RT Kit (QIAGEN, Valencia, Calif.). Primers for the Erbb2 (HER2 RT$^2$ qpCR primer assay, proprietary primer sequence, QIAGEN) and 18S housekeeping gene (forward: 5'-GG-GAGGTAGCGAAAAATAACAA-3' reverse: 5'-CCCTC-CAATGGATCCTCGTT-3') (IDT Inc, Coralville, Iowa) were used. The real-time PCR, in a reaction volume of 25 μL, was performed using the SYBR Green Supermix kit with the Bio-Rad iQ5 system (Hercules, Calif.). Denaturation at 95° C. for 15 seconds and annealing/extension (temperature varied due to different primer sequence and composition) for 1 min was performed for 40 cycles (FIG. 33).

In order to assess the metastatic state of the 4T1.2 Neu tumor model, after treatment with 17-DMAG, 60% acid-star polymer, star-GA, or no treatment, the visible axillary lymph nodes on the right side were harvested, measured, and analyzed by rtPCR. During the lymph node harvesting, gross visualization of the organs was made to identify any obvious signs of metastases, growths, or toxicities associated with any of the treatments.

All of the mice with the 4T1.2 Neu tumors exhibited significantly enlarged spleens at least twice the size of a normal mouse spleen. The mouse treated with star-GA (referred to in the previous section) with the low body score also appeared to have lung metastases and possible cardiac disease. One mouse that did not receive treatment also exhibited signs of cardiac disease. Finally, one mouse treated with the 17-DMAG appeared to have liver metastases. Before the lymph node samples were tested for HER2 expression by rtPCR to assess their metastatic state, the lymph nodes were measured with digital calipers and the axillary lymph node volumes were calculated using the same equation used to calculate tumor volume=$0.52\times(\text{width})^2\times(\text{length})$. Although there are noticeable differences in the axillary lymph node volumes, these differences are not statistical significant.

However, in these studies, the maximum deliverable dose of the star-GA was increased by 5-fold compared to that of i.v. 17-DMAG, with no visual signs of toxicity. Further pathological examination is needed to determine the overall treatment related toxicities associated with the administration of the star polymer and star-GA compared to the liver toxicities often associated with geldanamycin administration. Further immunohistopathology of the state of the enlarged spleens in this tumor model is worth investigating. In a similar 4T1 HER2 tumor model, both the spleen and livers were enlarged due to extramedullary hematopoiesis; further, the lungs (6/6), spleen (3/6) and liver (5/6) all exhibited metastases.

Typically when analyzing rtPCR data the amplification value of the target gene, HER2, would be normalized against the 18S housekeeping gene, however, the HER2 expression was very low in all of the axillary lymph node tissue samples for all treatment groups indicated by the average cycle threshold value of ca. 35; indicating that the axillary lymph nodes did not have HER2 expressing metastases. One animal in the star-GA treatment group did present a cycle threshold of ca. 29 for the HER2 expression; however, there were no statistically significant differences between the different treatment groups.

In addition to developing an intralymphatically delivered chemotherapeutic is the potential for reduction in the lymphatic metastatic potential. Although in vivo efficacy against the primary tumor growth of the 4T1.2 Neu tumor model was not observed, it is possible that the star-GA lymphatically targeted chemotherapeutic could prevent and/or treat lymphatic metastases. The 4T1.2 Neu tumor model is reported to be characteristic of spontaneous metastatic breast cancer with the formation of bone marrow metastasis within one week post implantation into the mammary fatpad. Where the 4T1 tumor model metastasize by both the lymphatic and hematological routes, with metastases in the draining lymph nodes, lungs, and liver. In order to investigate the metastatic state of the mice after treatment, the contralateral axillary lymph nodes were harvested, measured, and analyzed for the HER2 expression. No statistically significant differences were observed in the lymph node volume with all of the treatment groups; however, all of the axillary lymph nodes in the tumor bearing mice appeared to be enlarged compared to that of non-tumor-bearing mice. The HER2 expression was determined in the axillary lymph node samples; however, the HER2 expression was very low in all mice, suggesting that this tumor model was not metastatic at the end of this study.

It is possible that due to the limited size of the mice and the shear massiveness in the size of the tumors relative to the overall body size, that the primary tumor developed around or encompassed the metastatic lymph nodes, thus enabling their individual distinction for harvesting. Additional possibilities for the lack of HER2 expression in the axillary lymph nodes is that the tumor model did not reach a metastatic state by the end of the study (tumor volume=2000 mm$^3$), the metastatic cells "lost" their ability to express HER2 (as this was a transfected gene), or the tumor model was not as metastatic as it was originally presented in the reported tumor model.

Example 34

Synthesis of Multi-Arm Sugar Star Polymer-IR820 Conjugates

Figure 22:
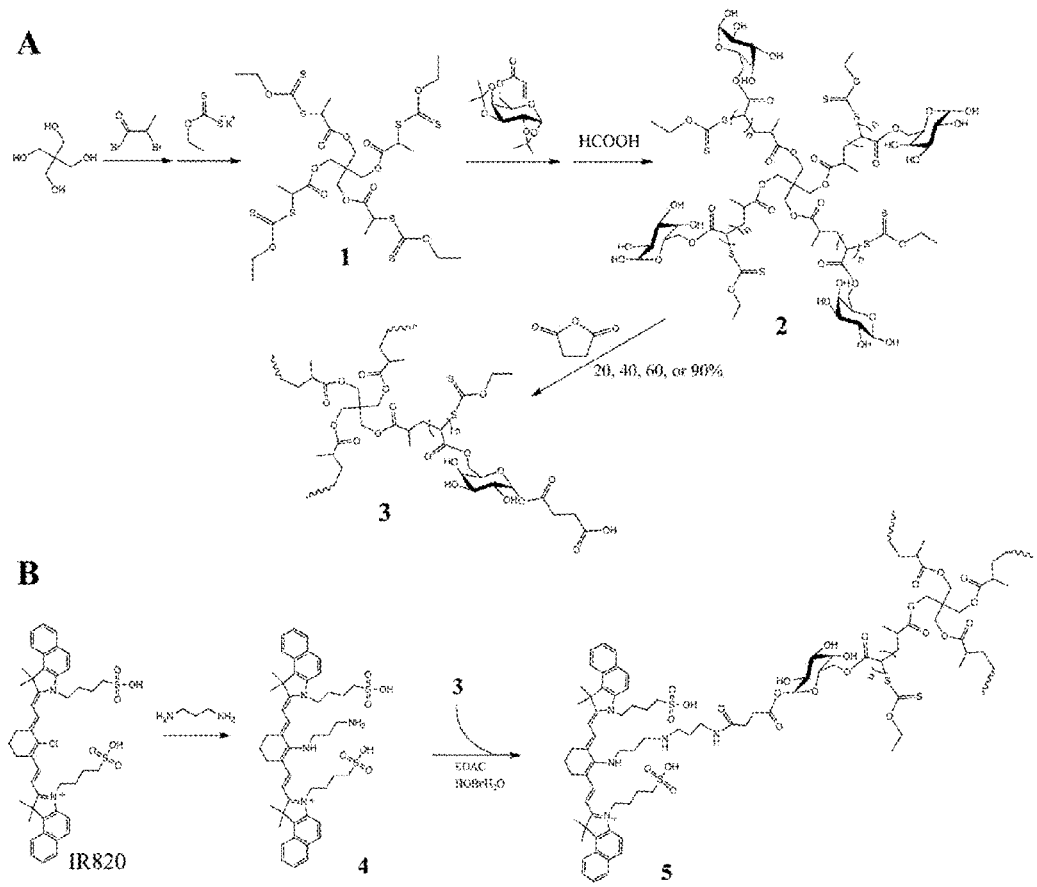
FIGS. 22A-22B include two schemes of the synthesis of the 4-arm sugar star polymers 2 by MADIX/RAFT polymerization and the subsequent modification with succinic anhydride to yield the 20, 40, 60, and 90% wt/wt sugar-acid star-polymers 3. Conjugation of 3-aminopropyl-amino-IR820 4 to a sugar-acid-star polymer 3 to yield the star-IR820 conjugate 5.

As shown in FIG. 22, a near-infrared dye, IR-820, was added to a series of multi-arm sugar star polymers with increasing degree of ionic character (20, 40, 60, and 90% succination) for in vivo imaging and reported in Table 7. For example, to a solution of IR-820 (100 mg, 0.094 mmol) in 20 ml dry DMF, 1,3-diaminopropane (40 µL, 0.47 mmol) was added dropwise. The solution was gradually heated to 60° C., and was allowed to react for 4 hours protected from light. The solvent was evaporated under reduced pressure followed purification by column chromatography (1:1 EtOAC: MeOH). The fractions were combined and the solvent was removed under reduced pressure, yielding a dark blue solid (65 mg, 78% yield). The 3-aminopropyl-amino-IR820 derivative 4 was conjugated to the sugar-acid star polymer 3 in dry DMF with EDAC activation and HOBt.$H_2O$ as the catalyst. A cooled solution (0° C.) of the sugar-acid-star polymer (60% acid) (75 mg) in 20 ml dry DMF, EDAC (28.1 mg, 0.147 mmol) and HOBt.$H_2O$ (22.5 mg, 0.147 mmol) were combined. After five minutes, the 3-aminopropyl-amino-IR820 derivative 4 (65 mg, 0.073 mmol) in DMF (5 ml) was added dropwise. The reaction was allowed to proceed at ambient temperature overnight and protected from light. The resulting sugar-acid-star-polymer-IR820 5 (star-IR820) was purified by dialysis (10,000 MWCO) against EtOH:$H_2O$ (1:1) followed by 100% EtOH. Concentration under reduced pressure resulted in a bluish-purple solid. The loading degrees of IR820 on the series of star polymers were determined by $^1$H NMR in MeOD.

TABLE 7

| % Acid | Polymer MW (kD) | wt % IR820 | # dyes/HA polymer |
|---|---|---|---|
| 20 | 54 | 7.8% | 5.3 |
| 40 | 63 | 6.8% | 5.3 |
| 60 | 72 | 5.2% | 4.6 |
| 90 | 85.5 | 8.6% | 9.3 |

Table 7 shows the IR820 loading degree on the various wt % acid modification for the multi-arm sugar star polymers.

Example 35

Figure 23:
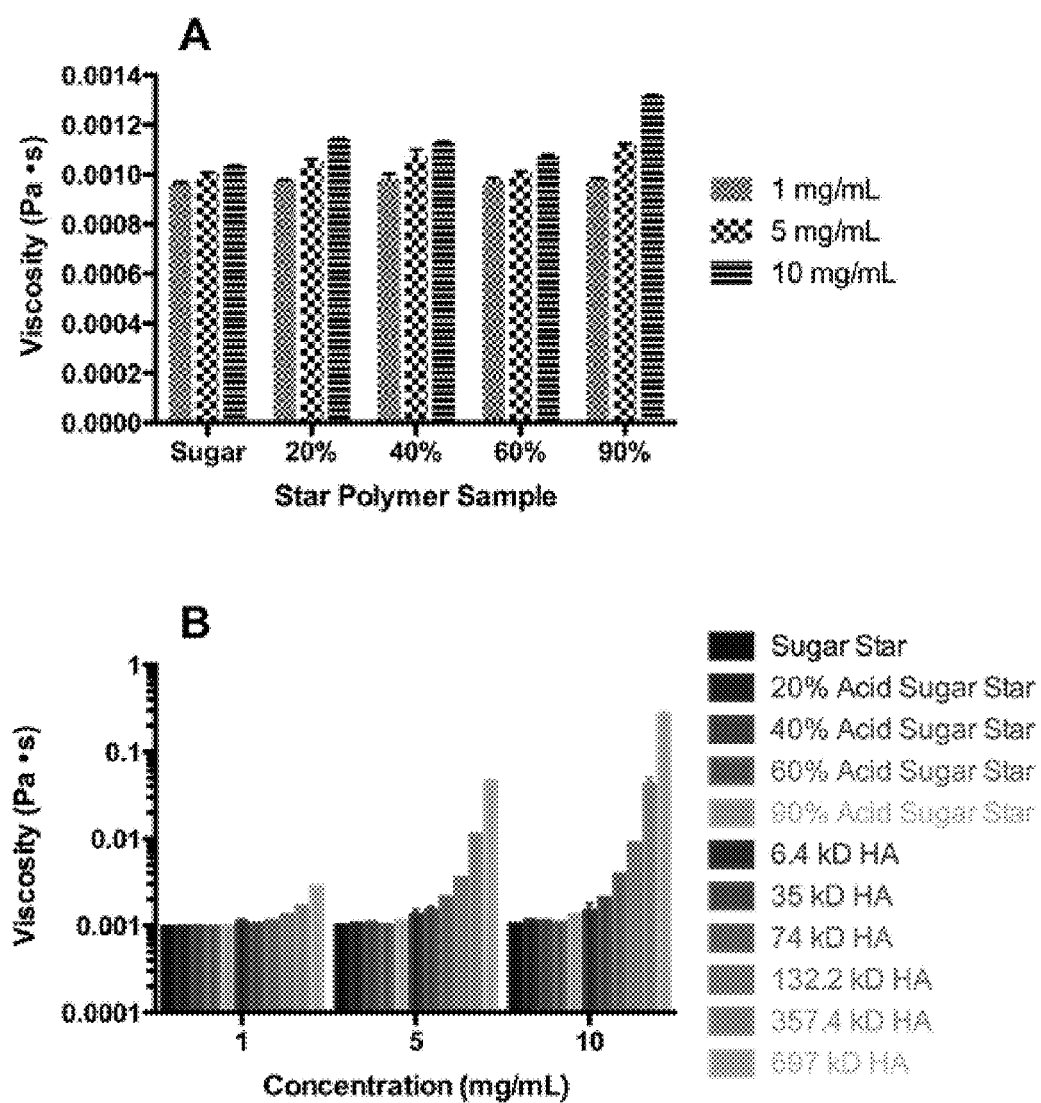
FIG. 23 includes two graphs of the viscosity measurement of the A) Viscosity of the sugar-star polymers in pH 7.4 PBS at a shear rate of 100 s$^{-1}$. B) Viscosity of hyaluronan (HA) and star polymers at 1, 5, and 10 mg/mL in PBS pH 7.4 at a shear rate of 100 s$^{-1}$ (n=3).

Viscosity of Multi-Arm Sugar Star Polymers with Increasing Degree of Ionic Character The viscosities of the acid star polymers were determined in PBS at pH 7.4, and reported in FIG. 23. For example, multi-arm sugar star polymer and multi-arm sugar acid star polymer samples were dissolved in PBS (at ca. 100 mg/ml conc.) and dialyzed against PBS (pH 7.4) for 48 hours at ambient temperature using a 3.5-kD MWCO dialysis tubing (regenerated cellulose, Fisherbrand) to adjust the pH. The star polymers were then diluted to 1, 5, and 10 mg/ml with PBS (pH 7.4) and the rheological properties were measured in triplicate using an Advanced Rheometer 2000 (TA Instruments, New Castle, Del.) at 25° C. using a 40-mm 2° aluminum cone geometry and a 49-µm gap distance. The shear rate was increased using a steady state flow step from 10 to 100 s$^{-1}$ with 10 points per decade using a log scale and a sample period of 10 s. The steady state parameters were set to 5% deviation for three consecutive points within a maximum time of 1 minute per shear rate.

The trends between the different star polymers with respect to increasing the concentration and MW on the apparent viscosity were determined by rheology. The viscosities of the star polymer samples in FIG. 23 represent the apparent viscosities of the polymers at a shear rate of 100 s$^{-1}$. The data obtained for the other shear rates exhibited the same trends as presented in FIG. 23 for a shear rate of 100 s$^{-1}$; however, the star polymer did appear to undergo minimal shear thinning over the shear rates examined. As the concentration increases, for each individual sugar or sugar-acid star polymer, the apparent viscosity also increases. However, as the MW is increased (sugar <20%<40%<60%<90%) at a given concentration, the apparent viscosity remains relatively constant.

Example 36

Zeta Potential of the Multi-Arm Sugar Star Polymers

Figure 24:
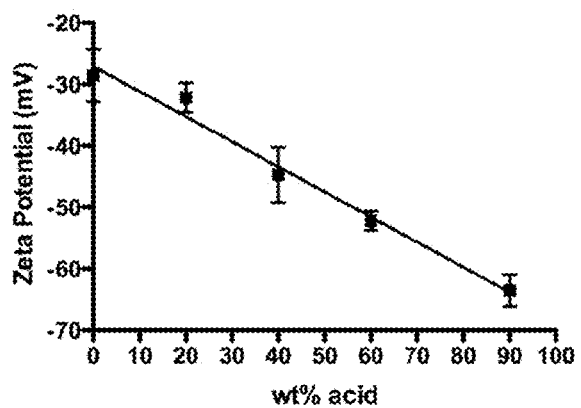
FIG. 24 includes a graph of the zeta potentials of the different wt % acid multi-arm sugar star polymers at 20° C., in a 1-mM phosphate buffer (pH 7.25) with 1-mM KCl ($R^2$=0.983).

The zeta potentials of multi-arm sugar star polymers were measured and reported in FIG. 24. For example, sugar-star and sugar-acid-star polymer samples were dissolved in dd$H_2O$ to a concentration of ca. 1 mg/ml, the pH was then adjusted to 7.2±0.1 with 1-N sodium hydroxide, and the final concentration was noted. The samples then were diluted to 100 µg/ml with pH 7.25 1-mM phosphate buffer with the addition of 1 mM of KCl. After dilution the pH was rechecked. Zeta potentials were measured on a ZetaPALS (Brookhaven Instruments Corporation, Holtsville, N.Y.) at 20° C. and the sample measurements were repeated six times.

The zeta potential increased linearly with wt % substitution of acid on star polymers ($R^2$=0.983). The zeta potentials of the star polymer samples were determined at pH 7.4 to ensure that all of the carboxylic acid functional groups were fully ionized (p$K_a$ ca. 4-5), which minimizes effects due to partial protonation of the carboxylic acids. Partial protonation would lead to minor changes in the pH, and a reduction in the double layer thickness leading to zeta potentials of lower magnitude than for fully ionized polymers. Further, the pH studied would be indicative of the ionization state in vivo, thus leading to biologically relevant zeta potentials for the star polymers.

Example 37

In Vitro Toxicity of the Multi-Arm Sugar Star Polymers

The cancer cell lines B16F10 (lymphatically metastatic murine melanoma, ATCC), MDA-MB-231 (human breast cancer), MDA-1986 (human head and neck squamous cell carcinoma), and HUVEC (normal human endothelial) cell lines, were maintained in Dulbecco's modified Eagle's medium (DMEM) supplemented with 1% L-Glutamine and 10% bovine growth serum in 5% $CO_2$ atmosphere. The HER2 expressing murine breast cancer cell line, 4T1.2 Neu, was a gift from Dr. Zhaoyang You, from the University of Pittsburg, and was maintained in DMEM supplemented with 1% L-Glutamine, 10% bovine growth serum, and 500 µg/ml of G418 (geneticin) in 5% $CO_2$ atmosphere. The lymphatically metastatic human melanoma cell line, A2058, was purchased from ATCC, and was maintained in low sodium bicarbonate DMEM (ATCC) supplemented with 1% L-Glutamine, and 10% bovine growth serum in 5% $CO_2$ atmosphere.

The sugar-acid star polymer samples (20, 40, 60, and 90 wt % acid) were dialyzed against PBS (as described in rheometry section) for 48 hours to adjust the pH to 7.4. The solutions were concentrated to ca. 100 mg/ml using a Speedvac concentrator (Labconoco) and diluted in sterile 1×PBS (Fisher BioReagents, pH 7.4) to eight concentrations between $10^{-4}$ to $10^{-9}$ M. Prior to cell growth inhibition studies, cells were trypsinized and seeded at 3000 cells/well in 96-well tissue culture treated plates. After 24 hours, the 20%, 40%, 60%, and 90% acid multi-arm sugar star polymers in PBS were added to the HUVEC, A2058, and 4T1.2 Neu cells (n=8, 10 µL/well, 8 concentrations). Only the 60% acid multi-arm sugar star polymer sample was added to the B16F10, MDA-MB-231, and MDA-1986 cells 24 hours after seeding (n=8, 10 µL/well, 8 concentrations). A solution of 10% trichloracetic acid was used as a negative control, and media was used as a positive control (n=8, 10 µL/well). At 72 hours post addition, 10 µL of resazurin blue in PBS was added (5-1 µM final concentration) to each well and the well fluorescence was measured after 3 hours a ($\lambda_{ex}/\lambda_{em}$=560/590 nm) (SpectraMax Gemini, Molecular Devices, USA). $IC_{50}$s were determined using the nonlinear regression curve fit for a one-site competition (GraphPad Prism 5), and reported in Table 8.

All four of the multi-arm sugar-acid star polymers had similar low anti-proliferative activity in all of the cell lines examined including normal and cancer cell lines, with the exception of the 60% acid multi-arm sugar star polymer in the MDA-1986 cancer cells, which exhibited a 10-fold increase in toxicity compared to the other cell lines.

Due to the intense fluorescence signal from the injection site saturating the camera, the injection area was covered with a piece of black tape allowing the visualization of the draining lymphatic vessels and lymph nodes. Images were acquired using the autoexposure function, which limits the pixel saturation to <2%, and exposure times were recorded. The use of the autoexposure function resulted in different exposure times for each image, which were corrected for using the scaled counts/s calculated by the software during the image analysis.

The four multi-arm sugar-acid-star-IR820 conjugates are approximately the same molecular weight but have various degrees of anionic charges and a wide zeta potential distribution. The differences in the lymphatic uptake of the multi-arm star polymers after s.c. administration are governed by the effect of charge rather than size. Drainage from the injection site occurs at similar rates for all four of the multi-arm sugar-acid-star-IR820 conjugates, as indicated by the same $t_{max}$ (time to reach maximal fluorescence signal) of 45 minutes. In another study in which a series of different MW hyaluronan polymers with the same charge were used, the $t_{max}$ increased with polymer MW.

The drainage kinetics to the popliteal and iliac nodes of the multi-arm acid-star-IR820 conjugates post s.c. administration are presented in FIGS. 4A and B, respectively. The

TABLE 8

| wt % Acid | HUVEC | A2058 | 4T1.2 Neu | B16F10 | MDA1986 | MDA-MB-231 |
|---|---|---|---|---|---|---|
| 20 | ~50 µM (2.7 mg/mL) | ~50 µM (2.7 mg/mL) | ~50 µM (2.7 mg/mL) | — | — | — |
| 40 | ~55 µM (3.5 mg/mL) | ~40 µM (2.5 mg/mL) | ~50 µM (3.2 mg/mL) | — | — | — |
| 60 | ~100 µM (7.2 mg/mL) | ~60 µM (4.3 mg/mL) | ~100 µM (7.2 mg/mL) | >100 µM (7.2 mg/mL) | 10 µM (0.72 mg/mL) | ≥100 µM (7.2 mg/mL) |
| 90 | ~55 µM (4.7 mg/mL) | ~50 µM (4.3 mg/mL) | ~55 µM (4.7 mg/mL) | — | — | — |

Table 8 shows the $IC_{50}$ values of the multi-arm sugar-acid star polymers in various cell lines post 72-hour incubation.

Example 38

In Vivo Imaging of Multi-Arm Sugar Star Polymer-IR820

Figure 25:
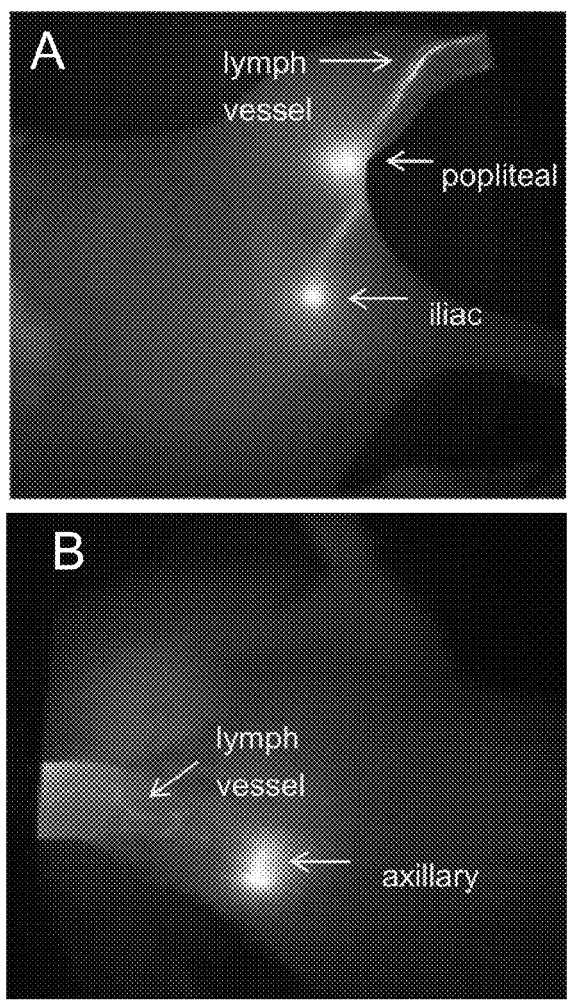
FIGS. 25A-25B include two fluorescent images after subcutaneous injections into the footpad and forearm of two Balb/C mice of 74 kDa star polymer-IR820 conjugates.

Animals were maintained in sterile housing under the veterinary supervision of the University of Kansas Animal Care Unit. All procedures were approved by the Institutional Animal Care and Use Committee. All mice were fed a low chlorophyll diet (Harlan 2918 irradiated diet) for at least one week prior to imaging to decrease food induced organ and skin autofluorescence. The mouse's hair in the area of interest for imaging was removed 24 hours prior to imaging with clippers followed by depilatory cream. Female Balb/c mice (20-25 g, Charles River) (3 per group) were anesthetized under isoflurane, placed on a heating pad to help regulate body temperature, and were injected subcutaneously (s.c.) with 10 µL of a filter-sterilized 0.1-mg/ml (IR820 dye conc.) solution of star-IR820 conjugates (20%, 40%, 60%, and 90% multi-arm acid-star-IR820) in the center of the right hind footpad (FIG. 25). The mice were imaged from both the dorsal and right sides, both with and without the injection site being covered, for a maximum of 7 days using whole body fluorescence imaging (Cambridge Research and Instrumentation Maestro multi-spectrum imager, Woburn, Mass.) using an excitation filter of 710-760 nm and broadpass emission filter of 800-950 nm. Animals were not imaged for more than 5 minutes during any single session.

kinetic profile for the lymphatic drainage of the 20% multi-arm acid-star-IR820 conjugate to both the popliteal and iliac nodes indicates that the 20% multi-arm acid-star-IR820 conjugate has statistically lower lymphatic uptake and increased retention in the popliteal and iliac lymph nodes over the length of the study compared to the 40, 60, and 90% multi-arm acid-star-IR820 conjugates (popliteal node, p<0.05, <0.0001, and <0.001, for the 40, 60, and 90% acid, respectively; iliac node, p<0.0001 for all three conjugates). The 20% acid multi-arm conjugate is highly retained at the injection site and the popliteal node, as indicated by the lower maximum fluorescence signal and longer $t_{50\%}$ (time required for the fluorescence signal to reduce by 50%).

Over the first 24 and 6 hours, the kinetic profiles for the lymphatic drainage to the popliteal node of the 40 and 90% acid-multi-arm star-IR820 conjugates were significantly different than that of the 60% acid-multi-arm star conjugate (p<0.05), as indicated by its significantly shorter $t_{50\%}$. Whereas, the 40 and 90% acid-multi-arm star-IR820 conjugates did not exhibit any significant differences in their lymphatic uptake to the popliteal node, which both have similar $t_{50\%}$ values. The kinetic profiles for the lymphatic uptake to the iliac node revealed slightly different trends compared to the popliteal node. The 90% acid-multi-arm star-IR820 conjugate profile was statistically different than the 40 and 60% acid-multi-arm star-IR820 conjugates over the first 24 and 50 hours, respectively (p<0.05), in that the 90% acid-multi-arm star-IR820 conjugate exhibited the shortest $t_{max}$ and a longer $t_{50\%}$ than for the 40 and 60% multi-arm conjugates which had similar $t_{50\%}$ and $t_{max}$ values.

The 40-90% acid-multi-arm star-IR820 conjugates exhibit remarkably different nodal retentions in the popliteal and iliac lymph nodes. The 60% acid-multi-arm star-IR820 cleared rapidly from the popliteal node compared to the other conjugates as indicated by the short $t_{50\%}$, but was retained in the iliac node for almost a day. In contrast, the 40% and 90% acid-multi-arm star-IR820 conjugates have similar popliteal $t_{50\%}$ values of ca. 7 hours, but the 90% acid-multi-arm star-IR820 was retained two times longer in the iliac node in comparison with 40% and 60% acid-multi-arm star-IR820 conjugates. Further, the 20% acid-multi-arm star-IR820 conjugate was highly retained in both the popliteal and iliac nodes compared to its more anionic counterparts as demonstrated by its longer $t_{50\%}$ values. However, the distribution of the AUC for the different degrees of anionic charge was similar for both the popliteal and iliac nodes. The 40-90% acid-multi-arm star-IR820 conjugates exhibited a 2.5- to 3.5-fold increase in the lymphatic uptake compared to the 20% acid-star-IR820 conjugate for both the popliteal and iliac nodes.

Example 39

In Vivo Imaging Data Analysis

Figure 26:
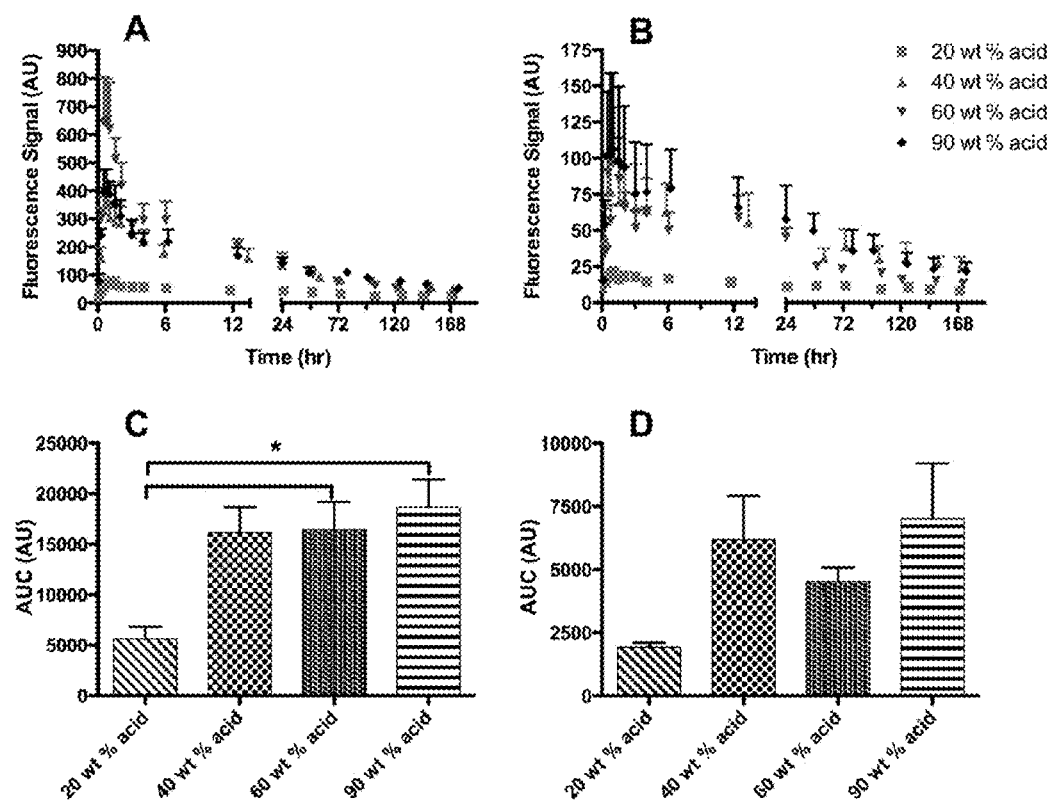
FIGS. 26A-26D include four graphs illustrating the drainage of Star-IR820 to the popliteal (A & C) and iliac (B & D) lymph nodes of mice.

Image analysis was performed using Maestro software (ver. 2.10). Regions of interest (ROI) were placed over the popliteal and iliac lymph nodes (FIG. 26 and Table 9). The total signal (scaled counts/s, see equation below as described by the Maestro software) intensity values (arbitrary units, AU) were recorded for each ROI, for both positions (prone and right), and were graphed versus time in GraphPad Prism (ver. 4). In addition, the area under the curve (AUC) was determined from the total fluorescence intensity vs. time graphs. Comparisons between multiple groups were made with one-way ANOVA analysis with a Tukey Multiple Comparisons post-test.

$$\text{Scaled counts}/s = \text{counts/full scale} \times 1/\exp(s) \times 1/\text{bin}^2 \times 1/\text{gain}$$

TABLE 9

| wt % Acid | Popliteal $t_{max}$ (min) | Popliteal $t_{50\%}$ (hr) | Iliac $t_{max}$ (hr) | Iliac $t_{50\%}$ (hr) |
|---|---|---|---|---|
| 20 | 45-50 | 19.5 | 1 | 113.6 |
| 40 | 45-50 | 6.9 | 2 | 18.6 |
| 60 | 45-50 | 1.9 | 1 | 19 |
| 90 | 45-50 | 7.7 | 0.5 | 40 |

Table 9 shows the IC$_{50}$ values of the sugar-acid star polymers in various cell lines post 72-hour incubation.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

What is claimed and desired to be secured by Letters Patent is as follows:

1. A multi-arm compound according to Formula 1:

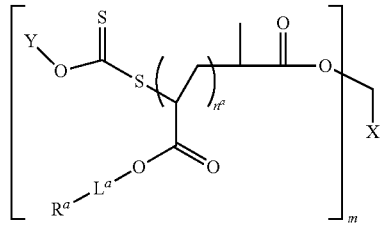

wherein:
X is one of carbon (C), oxygen (O), nitrogen (N), phosphorous (P), or sulfur (S);
m is 2, 3, 4, 5, 6, 7, or 8 and indicates a total number of arms;
Y is alkyl;
$L^a$ are each independently a bond or a linker;
$R^a$ are each independently a therapeutic agent, imaging agent, hydrogen, or combinations thereof;
$n^a$ are each independently an integer from 2 to 500;
a is a numerical character uniquely identifying each of said arms;
wherein when $R^a$ is hydrogen, $L^a$ is a bond;
wherein at least one of $R^a$ is a therapeutic agent, imaging agent, or combinations thereof; and
wherein at least one $L^a$ is a linker including one or more subunits having one or more sugars or carbohydrates.

2. The compounds of claim 1 wherein Y is ethyl such that the compounds may be defined according to Formula 1A:

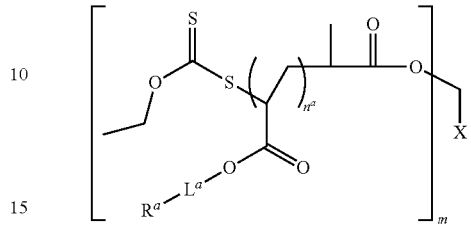

3. The compounds of claim 1 wherein
m is 4 such that the compounds have four arms;
$L^a$ is $L^1$, $L^2$, $L^3$, and $L^4$ in each arm, respectively;
$R^a$ is $R^1$, $R^2$, $R^4$, and $R^4$ in each arm, respectively;
$n^a$ is $n^1$, $n^2$, $n^3$, and $n^4$ in each arm, respectively;
such that the compounds may be defined according to Formula 1B:

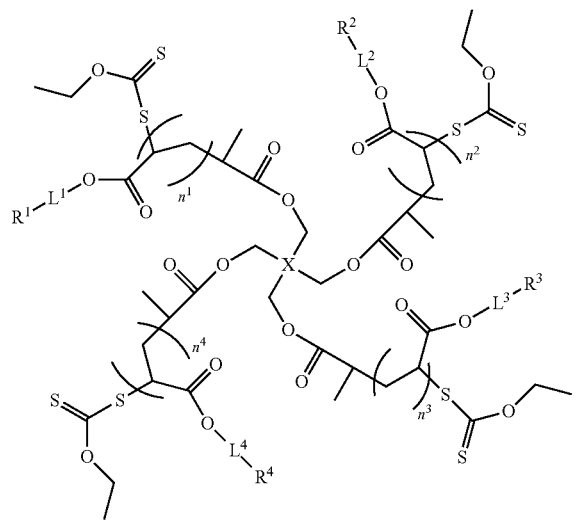

wherein:
X is one of carbon (C), phosphorous (P), or sulfur (S), and optionally has one or more additional arms each having a linker;
$L^1$-$L^4$ are each independently a bond or a linker;
$R^1$-$R^4$ are each independently a therapeutic agent, hydrogen, or imaging agent;
$n^1$-$n^4$ are each independently an integer from 2 to 500
wherein when $R^a$ is hydrogen, $L^a$ is a bond; and
wherein at least one of $R^a$ is a therapeutic agent or imaging agent.

4. The compounds of claim 3 wherein X is carbon such that the compounds may be defined according to Formula 1C:

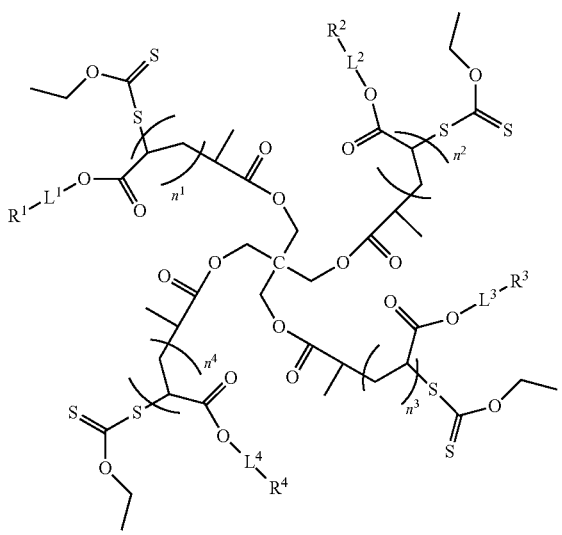

5. The compounds of claim 1 wherein $L^a$ are each independently a degradable linker having one or more of an ester, hydrazole, or ketal.

6. The compounds of claim 3 wherein $L^1$-$L^4$ are each independently a degradable linker having one or more of an ester, hydrazole, or ketal.

7. The compounds of claim 1 wherein at least one linker is a polymerization reaction product from one or more of a vinyl, amide, ester, alkyl, hydrazole, or ketal.

8. The compound of claim 1 wherein at least one linker includes one or more subunits having glucose, galactose, sucrose, lactose, glucuronic acid, N-acetylglucoamine, or combinations thereof.

9. The compounds of claim 3 wherein at least one linker includes one or more subunits having glucose, galactose, sucrose, lactose, glucuronic acid, N-acetylglucoamine, or combinations thereof.

10. The compounds of claim 3 wherein at least one linker includes a galactose having one or more carboxylic acids formed by addition of succinic acid to the galactose.

11. The compounds of claim 1 wherein $R^a$ is a therapeutic agent.

12. The compounds of claim 3 wherein $R^1$-$R^4$ is a therapeutic agent.

13. The compounds of claim 1 wherein $R^a$ is an imaging agent.

14. The compounds of claim 3 wherein $R^1$-$R^4$ is an imaging agent.

15. The compounds of claim 1 wherein $R^a$ is selected from the group consisting of JS-K, cisplatin, oxliplatin, carbolatin, doxorubicin, rapamysin, geldanamycin, alternol, TGX221, or nitric oxide donating prodrugs, any derivatives or analogs of the foregoing, or combinations thereof.

16. The compounds of claim 1 wherein $R^a$ is an nitric oxide donating prodrug according to:

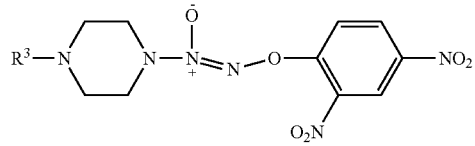

wherein $R^3$ is as hydroxylalkyl or hydroxyalkoxyalkyl.

17. The compounds of claim 3 wherein $R^1$-$R^4$ is selected from the group consisting of JS-K, cisplatin, oxliplatin, carbolatin, doxorubicin, rapamysin, geldanamycin, alternol, TGX221, or nitric oxide donating prodrugs, any derivatives or analogs of the foregoing, or combinations thereof.

18. The compounds of claim 1 wherein said compound has a dimension of about 5 nm to about 400 nm.

19. The compounds of claim 1 wherein the compounds have a molecular weight of about 10 kDa to about 1 MDa.

* * * * *